US008889640B1

(12) United States Patent
Smith et al.

(10) Patent No.: US 8,889,640 B1
(45) Date of Patent: Nov. 18, 2014

(54) COMPOSITION AND METHOD FOR THE TREATMENT OF GASTRIN MEDIATED CANCERS

(76) Inventors: Jill P. Smith, Camp Hill, PA (US); Mark Kester, Harrisburg, PA (US); Gail L. Matters, Hummelstown, PA (US); John F. Harms, Hershey, PA (US)

( * ) Notice: Subject to any disclaimer, the term of this patent is extended or adjusted under 35 U.S.C. 154(b) by 53 days.

(21) Appl. No.: 12/489,334

(22) Filed: Jun. 22, 2009

Related U.S. Application Data

(60) Provisional application No. 61/132,657, filed on Jun. 20, 2008.

(51) Int. Cl.
 *C12N 15/11* (2006.01)
(52) U.S. Cl.
 USPC ........................................................ 514/44 A
(58) Field of Classification Search
 USPC ....................................................... 514/44 A
 See application file for complete search history.

(56) References Cited

U.S. PATENT DOCUMENTS

2004/0248790 A1* 12/2004 Hinuma et al. ................. 514/12
2006/0240093 A1* 10/2006 MacLachlan et al. ........ 424/450

FOREIGN PATENT DOCUMENTS

WO    WO2006/016275 A2 *  2/2006

OTHER PUBLICATIONS

Harms et al. Pancreas, 33, Nov. 2006, pp. 466-467.*
Harms et al. Gastroenterology, 132, p. A424, Apr. 2007.*
Tuschl (The siRNA user guide, pp. 1-5, 2001).*
BPAI 2011-009971, U.S. Appl. No. 11/083,583, pp. 1-11, Nov. 28, 2012.*

* cited by examiner

*Primary Examiner* — Brian Whiteman
(74) *Attorney, Agent, or Firm* — Laurence A. Weinberger

(57) ABSTRACT

Gastrin mRNA down-regulation using either stable transfection of an antisense gastrin cDNA or one of three shRNA (short hairpin RNA) constructs achieves significant reduction in growth of human pancreatic cancer. Tumor growth rate and incidence of metastases in both wild type and transfected pancreatic cancer cells is directly proportional to the degrees of gastrin mRNA expression. In order to avoid rapid degradation of injected siRNA, nanoliposomes can be loaded with gastrin siRNA and used to deliver the siRNA to the tumors. Significant reduction of tumors in mice using siRNA loaded nanoliposomes is achieved. Uptake of pegylated nanoliposomes by tumor cells depends upon the pegylation percentage.

6 Claims, 17 Drawing Sheets

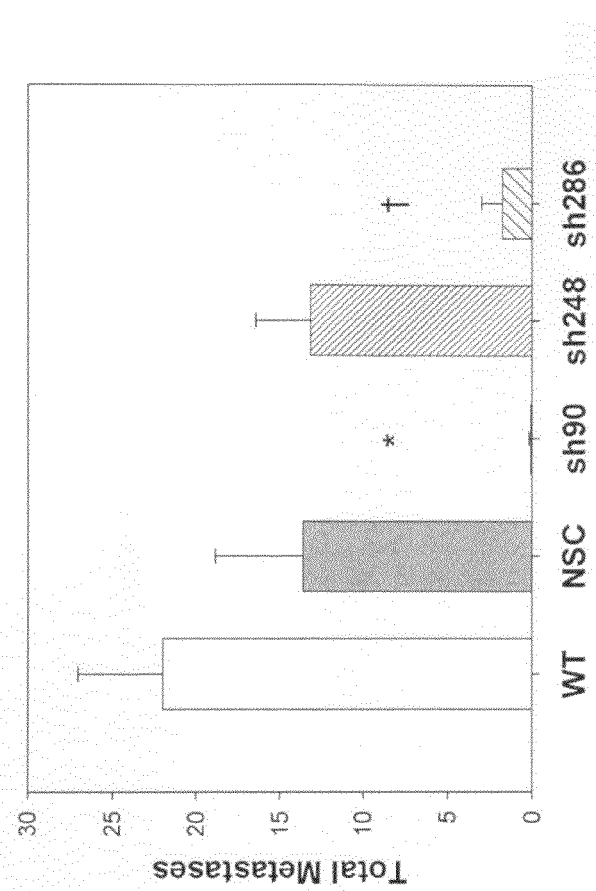
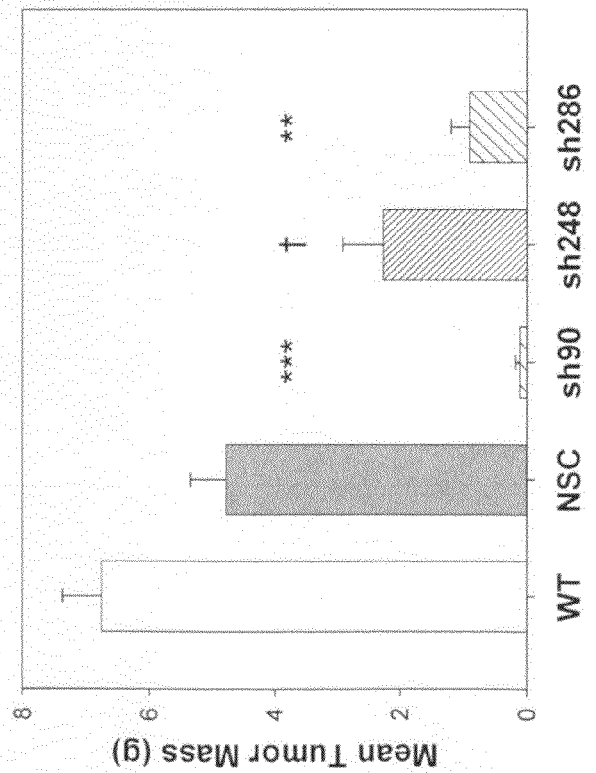
FIG.5D
FIG.5C

Formula RC 0.5%peg
11-18-04    10mg/ml         r6:3:1

| Lipid | IW (mg/mmol) | Mg Lipid | umol | Molar Ratio | Stock (mg/ml) | ul (1ml) |
|---|---|---|---|---|---|---|
| DOTAP | 774.19 | 5.0063 | 6.4665 | 4.975 | 25 | 200.25 |
| PEG(2000)-DSPE | 2,805.54 | 0.1823 | 0.0650 | 0.05 | 25 | 7.29 |
| DOPE | 744.04 | 4.8113 | 6.4665 | 4.975 | 25 | 192.45 |
| Total | x | 10.0000 | 12.9980 | 10 | 10 | 400.00 |

Formula RC 1.25%peg
11-18-04    10mg/ml         r6:3:1

| Lipid | IW (mg/mmol) | Mg Lipid | umol | Molar Ratio | Stock (mg/ml) | ul (1ml) |
|---|---|---|---|---|---|---|
| DOTAP | 774.19 | 4.8714 | 6.2922 | 4.937 | 25 | 194.86 |
| PEG(2000)-DSPE | 2,805.54 | 0.4470 | 0.1593 | 0.125 | 25 | 17.88 |
| DOPE | 744.04 | 4.6817 | 6.2922 | 4.937 | 25 | 187.27 |
| Total | x | 10.0000 | 12.7438 | 10.00 | 10 | 400.00 |

Formula RC 2.5%peg
11-18-04    10mg/ml         r6:3:1

| Lipid | IW (mg/mmol) | Mg Lipid | umol | Molar Ratio | Stock (mg/ml) | ul (1ml) |
|---|---|---|---|---|---|---|
| DOTAP | 774.19 | 4.6579 | 6.0165 | 4.875 | 25 | 186.32 |
| PEG(2000)-DSPE | 2,805.54 | 0.8656 | 0.3085 | 0.25 | 25 | 34.62 |
| DOPE | 744.04 | 4.4765 | 6.0165 | 4.875 | 25 | 179.06 |
| Total | x | 10.0000 | 12.3415 | 10 | 10 | 400.00 |

Formula RC 3.75%peg
11-18-04    10mg/ml         r6:3:1

| Lipid | IW (mg/mmol) | Mg Lipid | umol | Molar Ratio | Stock (mg/ml) | ul (1ml) |
|---|---|---|---|---|---|---|
| DOTAP | 774.19 | 11.3405 | 14.6482 | 4.838 | 25 | 453.62 |
| PEG(2000)-DSPE | 2,805.54 | 2.7607 | 0.9840 | 0.325 | 25 | 110.43 |
| DOPE | 744.04 | 10.8988 | 14.6482 | 4.838 | 25 | 435.95 |
| Total | x | 25.0000 | 30.2804 | 10.00 | 25 | 1000.00 |

Formula RC    i.e. 5%
11-18-04    10mg/ml         r6:3:1

| Lipid | IW (mg/mmol) | Mg Lipid | umol | Molar Ratio | Stock (mg/ml) | ul (1ml) |
|---|---|---|---|---|---|---|
| DOTAP | 774.19 | 4.2689 | 5.5141 | 4.75 | 25 | 170.76 |
| PEG(2000)-DSPE | 2,805.54 | 1.6284 | 0.5804 | 0.5 | 25 | 65.14 |
| DOPE | 744.04 | 4.1027 | 5.5141 | 4.75 | 25 | 164.11 |
| Total | x | 10.0000 | 11.6085 | 25 | 10 | 400.00 |

FIG.8A

COMPOSITION AND METHOD FOR THE TREATMENT OF GASTRIN MEDIATED CANCERS

Benefit of U.S. Provisional Application No. 61/132,657 filed on Jun. 20, 2008 is hereby claimed.

BACKGROUND OF THE INVENTION

1. Field of the Invention

High levels of gastrin production are associated with autocrine pancreatic tumors. Gastrin levels and growth of human pancreatic cancer can be down-regulated by employing miRNA.

2. Description of Related Art

The gastrointestinal peptide gastrin is involved in growth of the gastrointestinal tract[1,2]. In addition, gastrin has been shown to play a role in proliferation of several neoplasms, including colon cancer[3-6], gastric cancer[7,8], lung cancer[9], and pancreatic cancer[10-12]. Gastrin immunoreactivity is found in the fetal pancreas, but its expression is limited to the G-cells of the stomach in the adult[13]. Examination of cultured human pancreatic cancer cell lines has shown that gastrin is reexpressed in these cells and stimulates their growth by an autocrine mechanism[14]. Short-term administration of gastrin antisense oligonucleotides decreased cancer cell proliferation, further substantiating the endogenous role of gastrin on growth[14,15]. Selective radioimmunoassay further demonstrated that the form of gastrin produced endogenously in pancreatic cancer cells and tissues was consistent with the fully processed form, gastrin-17[16]. The fact that gastrin is produced by human pancreatic cancer cells suggests also a role for this peptide in development of pancreatic cancer. Knockdown of gastrin gene expression with an antisense gastrin cDNA decreases growth of human BxPC-3 pancreatic cancer xenografts grown subcutaneously in nude mice[17].

The mechanism by which gastrin exerts its trophic effects continues to be investigated. Gastrin, in various forms including fully processed and amidated gastrin, progastrin, or glycine-extended gastrin, has been shown to induce proliferation in several types of cancers[18]. The effect of gastrin is mediated through increased transcription of ligands of the EGF receptor (EGFR)[19,20], the REG protein[21], and cyclooxygenase-2[22]. Gastrin promotes growth and survival of rat AR4-2J pancreatic cancer cells by activating small GTP-binding proteins (Ras, Rac, Rho, and Cdc42), while the gastrin gene promoter is synergistically activated by the TGFβ/SMAD and Wnt signaling pathways[23,24]. Tomkova and colleagues have shown that the transcription factor p73, a homolog of the p53 tumor suppressor gene, binds to the gastrin gene promoter in human gastric cancer cells and increases transcription of gastrin mRNA[25]. In addition, gastrin has an anti-apoptotic effect through stimulation of PKB/Akt signaling and activation of NF-κB[26], and enhances angiogenesis via modulation of heparin-binding epidermal-like growth factor[27].

Gastrin has recently been a target for the development of anti-cancer therapeutics. Brett and coworkers[28] tested the efficacy of an anti-gastrin immunogen, G17DT, in pancreatic cancer patients and reported increased survival, however this occurred only in a sub-group of subjects that developed anti-gastrin antibodies. Gastrazole, a gastrin receptor antagonist, was given to advanced pancreatic cancer patients with an improvement in overall patient survival that was comparable to standard treatment of 5-FU[29]. When combined with gemcitabine, a newer orally active gastrin receptor antagonist (Z-360) has shown modest efficacy against orthotopic pancreatic tumors in mice[30]. Transient knockdown of gastrin gene expression by transfecting pancreatic cancer cells with antisense gastrin constructs[31] or with gastrin siRNA[32] decreased gastrin levels and tumor cell proliferation in vitro.

DESCRIPTION OF THE FIGURES

FIG. 1. Wild-type human pancreatic cancer cells have variable gastrin expression.

A: AsPC-1
B: BxPC-3
C: Capan-1
D: MIA PaCa-2
E: PANC-1
F: SW-1990
G: BxPC-3 control with secondary antibody only.

The corresponding bright field images ($A_1$-$G_1$) are shown for each cell type.

FIG. 3. Gastrin antisense and shRNAs decrease gastrin mRNA.

Figure 3A:
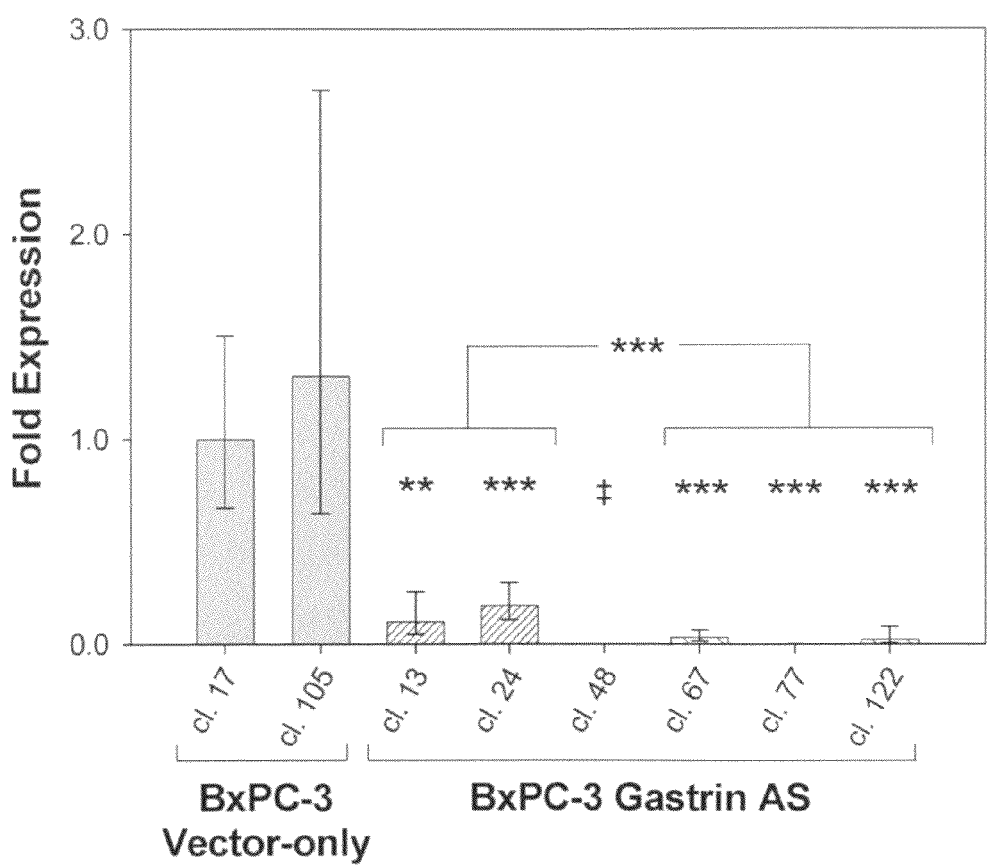

FIG. 3A. Real-time RT-PCR analysis of BxPC-3 clones transfected with a gastrin antisense construct (hatched bars) or empty vector control clones (solid bars). Columns represent the fold change in mRNA levels calculated from the mean relative quantity (RQ=$2^{-\Delta\Delta CT}$) and bars represent a 95% confidence interval (CI; RQ=$2^{-(\Delta\Delta CT \pm CI)}$).

Figure 3B:
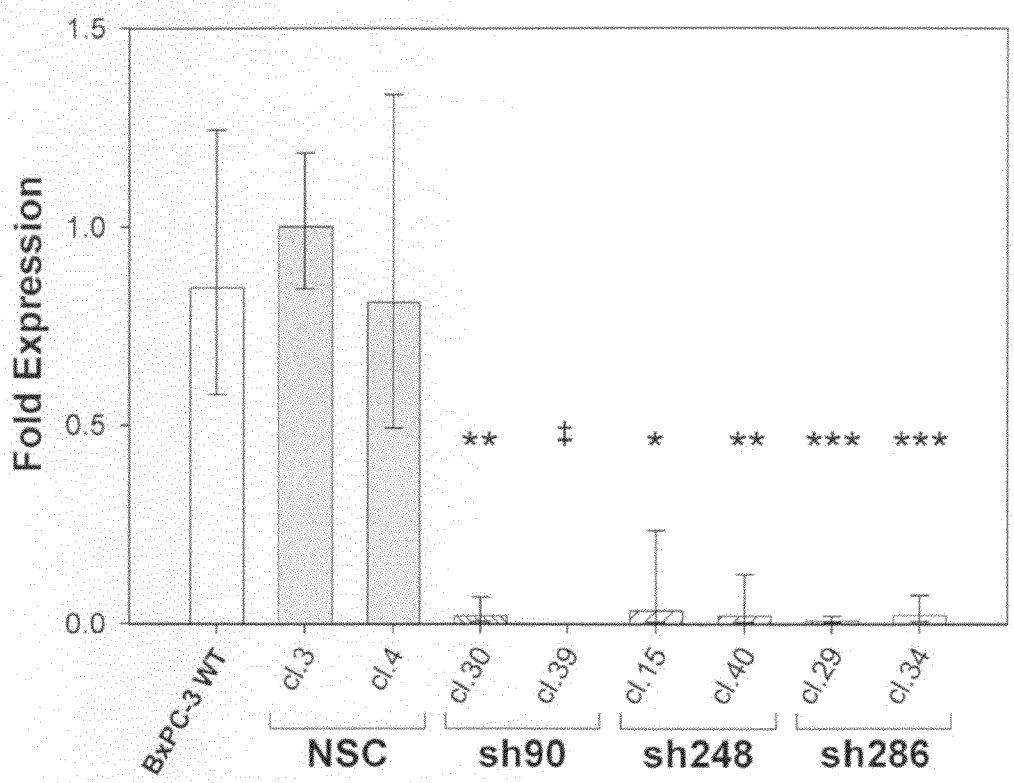

FIG. 3B. Gastrin mRNA levels measured by Real-Time RT-PCR in BxPC-3 clones independently transfected with three different gastrin shRNA constructs: sh90, sh248 and sh286 (hatched bars) as well as non-specific control transfectants (solid bars) and wild-type cells (open bar). Asterisks indicate values significantly different from controls at * p<0.01,  p<0.001, * p<0.0001 or ‡=undetected.

FIG. 4. Gastrin antisense and shRNAs decrease subcutaneous tumor growth.

Figure 4A:
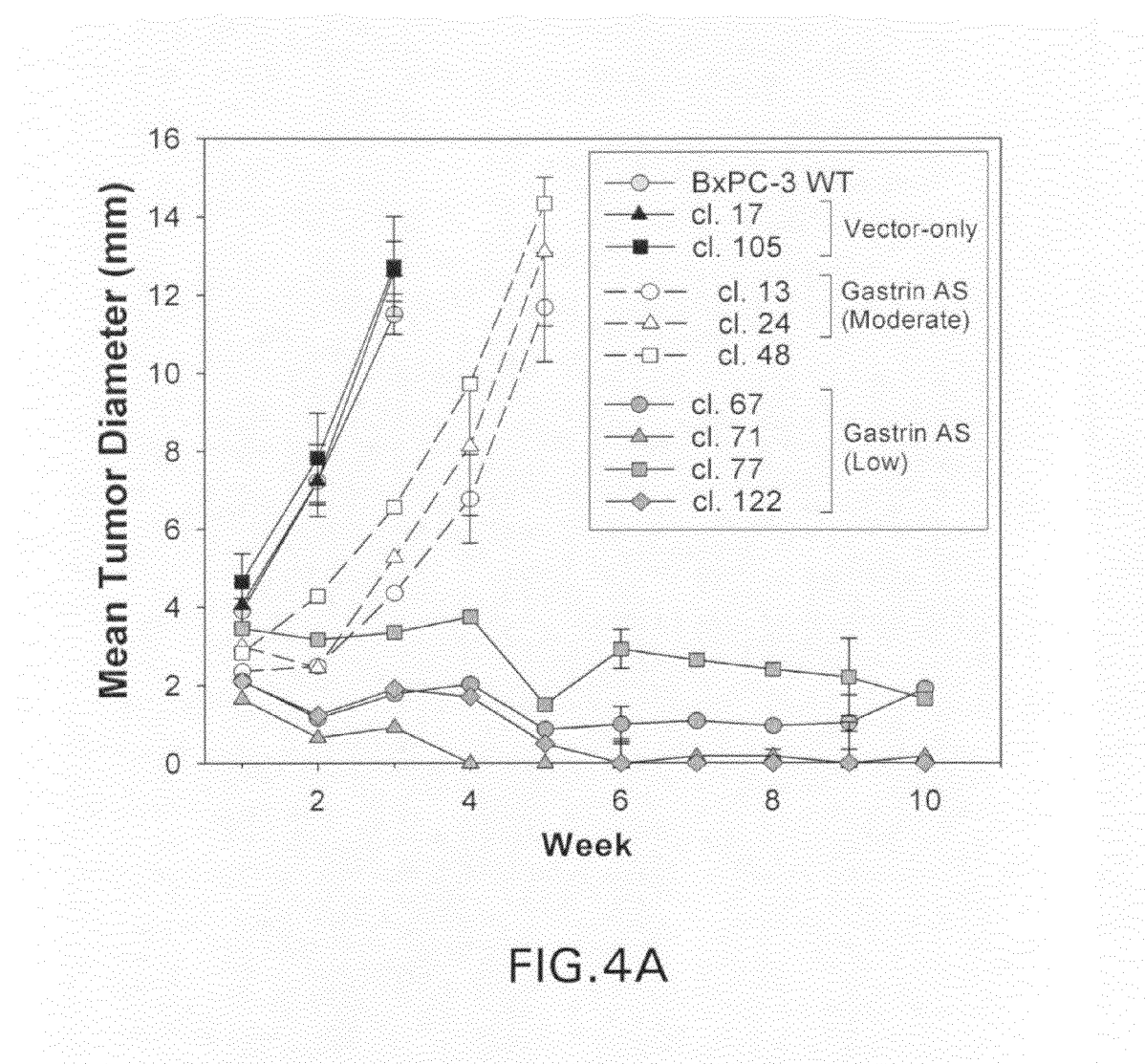

FIG. 4A. Growth of BxPC-3 subcutaneous tumors in nude mice measured weekly for up to 10 weeks. Mean tumor diameter (mm)±SEM was determined for wild-type BxPC-3 cells (open circles, solid line), vector-only clones (solid symbols, solid line), gastrin antisense clones with moderate gastrin expression (open symbols, dashed line) and gastrin antisense clones with low gastrin expression (shaded symbols, solid line).

Figure 4B:
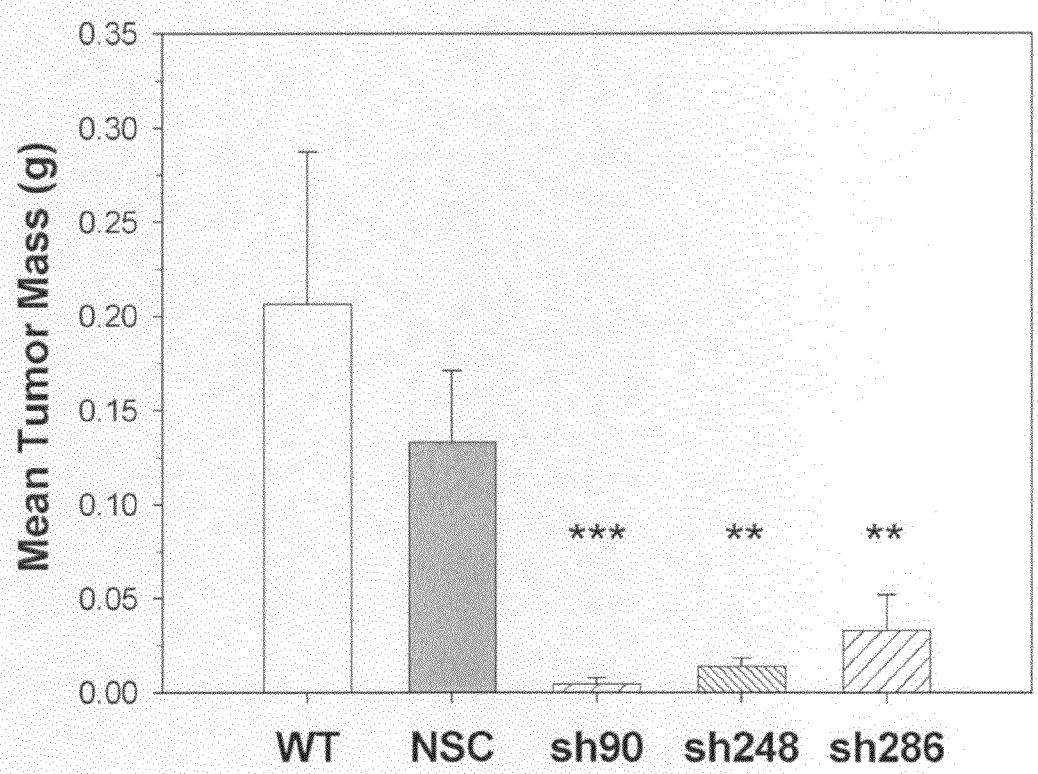

FIG. 4B. For gastrin shRNA clones and controls, subcutaneous tumor mass (g, mean±SEM) was measured 2 weeks after tumor cell injection (n=5-8 tumors). Multiple clones from three independent gastrin shRNA target sites (hatched bars) were compared to wild-type BxPC-3 cells (open bar) and non-specific shRNA clones (solid bar). Significant differences compared to controls are represented by  p<0.001, * p<0.0001.

FIG. 5. Gastrin antisense and shRNAs decrease orthotopic tumor growth and metastasis.

Figure 5A:
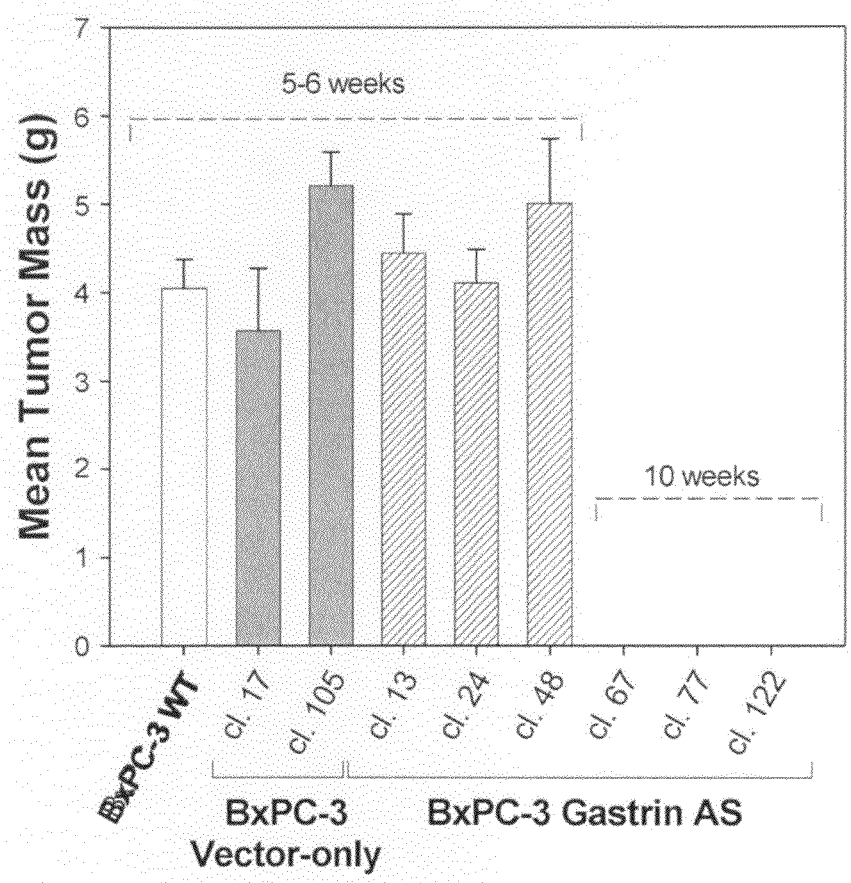

FIG. 5A. Mean orthotopic tumor mass in gastrin antisense clones compared to wild type and empty vector controls. Bars are mean mass in g±SEM of at least four independent tumors.

Figure 5B:
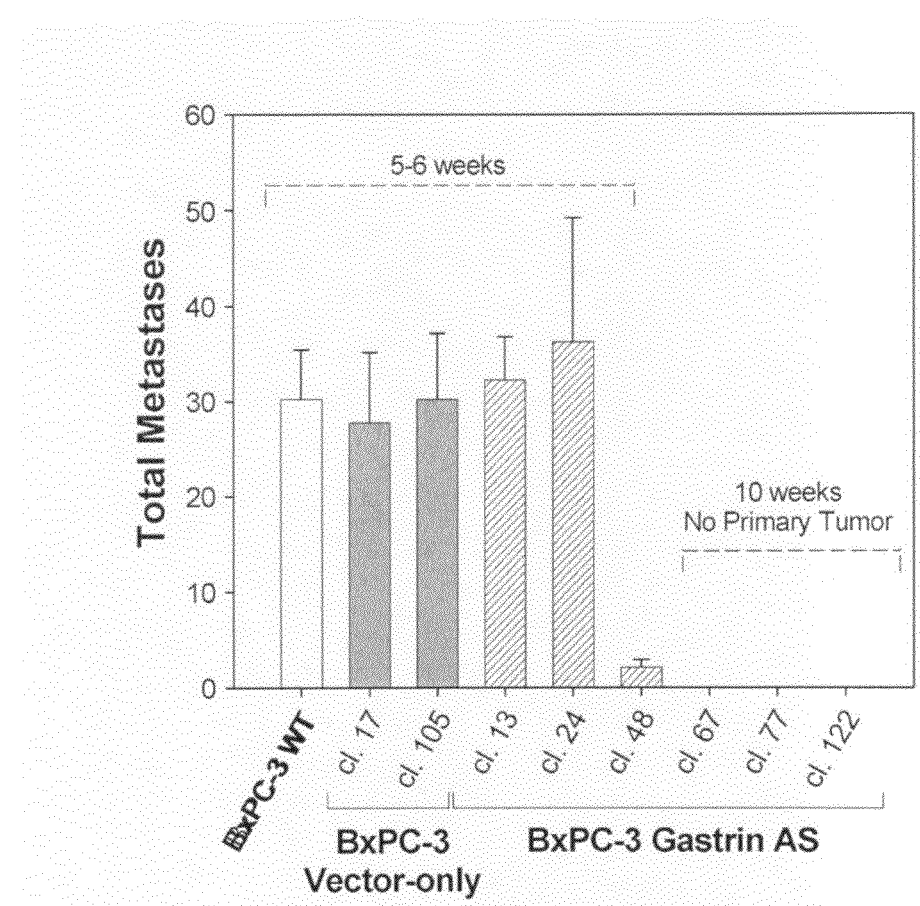

FIG. 5B. The number of metastases from the orthotopic tumor site in wild-type, nonspecific controls (NSC), or in gastrin antisense clones.

FIG. 5C. Mean orthotopic tumor mass in gastrin shRNA knockdown clones compared to wild type and NSC controls. Bars are mean mass in g±SEM of 4 to 6 independent tumors.

FIG. 5D. The number of metastases from the orthotopic tumor site in wild-type and nonspecific controls (NSC) or in gastrin sh90, sh248 or sh286 clones. Significant differences compared to controls are represented by †$p<0.05$, * $p<0.01$,  $p<0.001$, * $p<0.0001$.

Figure 6:
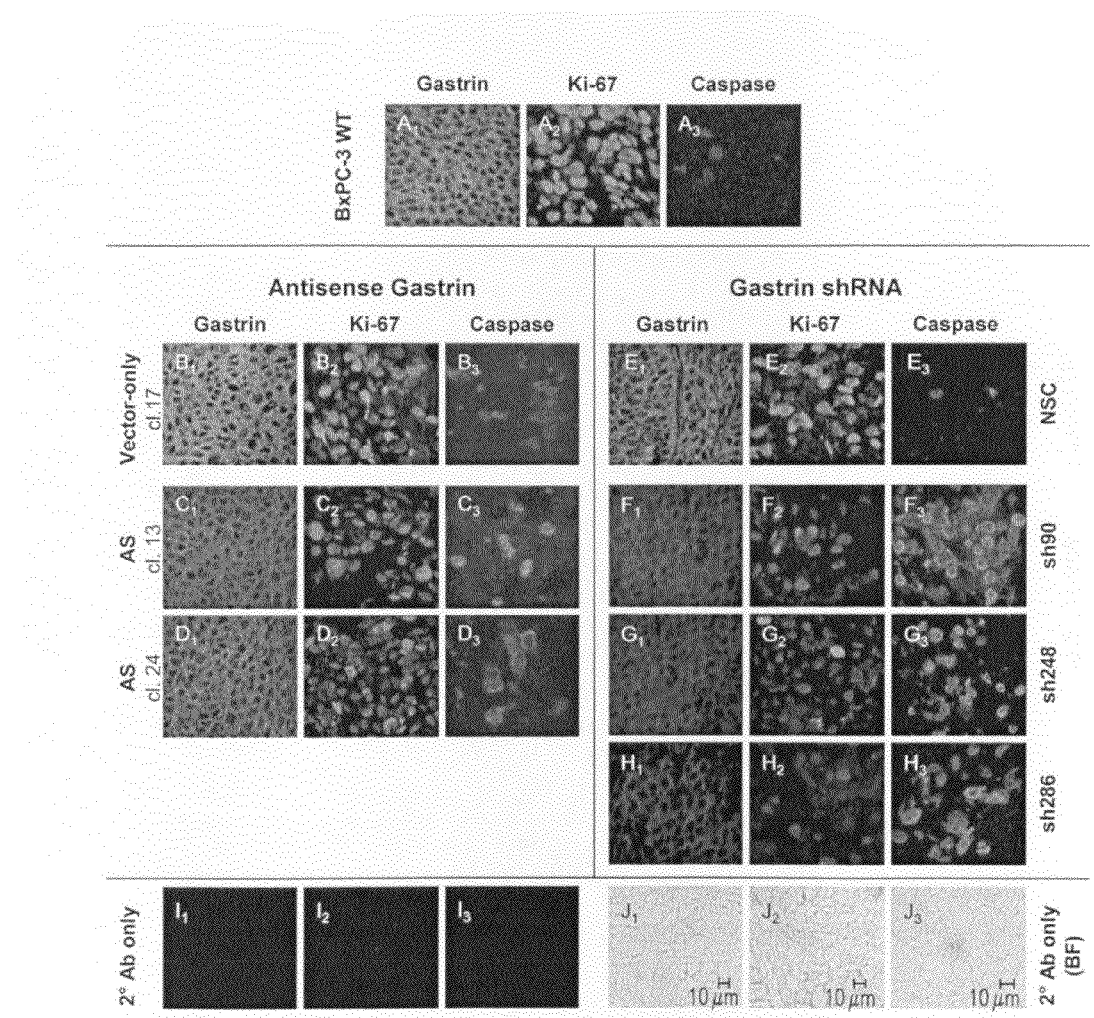

FIG. 6. Immunofluorescence staining for gastrin, Ki-67, and cleaved caspase-3 in BxPC-3 orthotopic tumors. Wild-type BxPC-3 cells and BxPC-3 clones expressing gastrin antisense constructs, gastrin shRNA constructs, or vector controls were grown in the pancreas of nude mice. Sections of the orthotopic tumors were reacted with a polyclonal rabbit anti-gastrin antibody (A1 to H1), a monoclonal mouse anti-human Ki-67 antibody (A2 to H2), or a polyclonal anti-human cleaved caspase-3 antibody (A3 to H3). Secondary antibody only controls are shown in I1 to I3, and corresponding bright field photos for the secondary only controls are shown in J1 to J3.

FIG. 7. Gastrin siRNAs decrease gastrin mRNA in pancreatic cancer cells in vitro and gastrin siRNA loaded nanoliposomes decrease growth of pancreatic tumors in vivo.

Figure 7A:
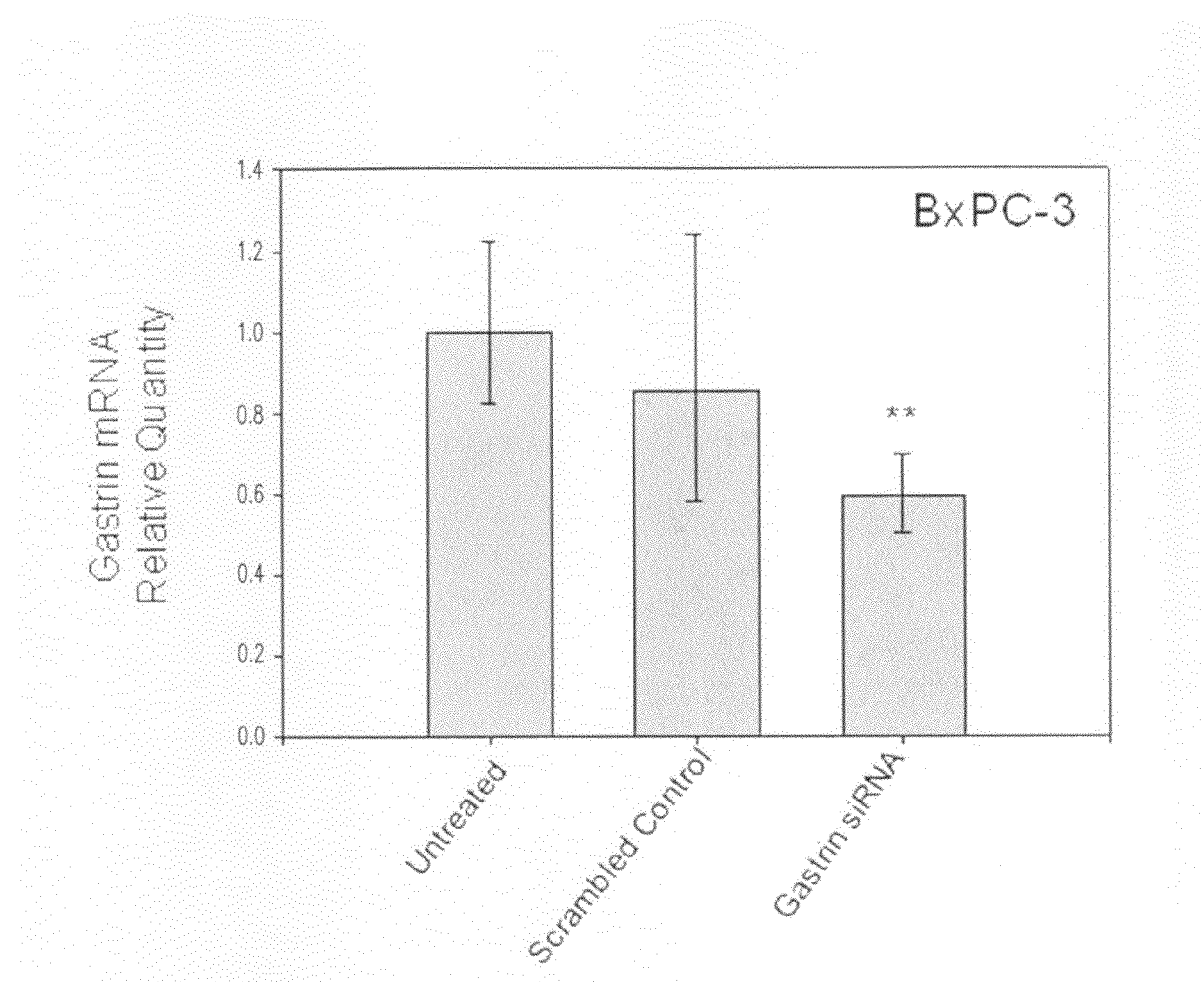

FIG. 7A. Real-Time RT-PCR quantitation of gastrin mRNA levels in untreated BxPC-3 cells or in BxPC-3 cells treated with nanoliposome loaded with either gastrin siRNA286 or scrambled control siRNA. Only cells treated with the gastrin siRNA had reduced gastrin mRNA levels compared to untreated cells (** $p<0.001$)

Figure 7B:
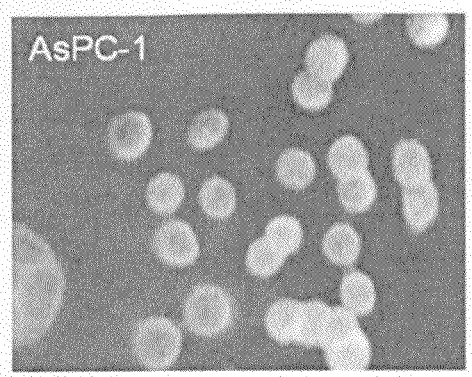

FIG. 7B. AsPC-1 cells treated for 1 hr with rhodamine-labeled nanoliposomes and visualized by fluorescence microscopy.

Figure 7C:
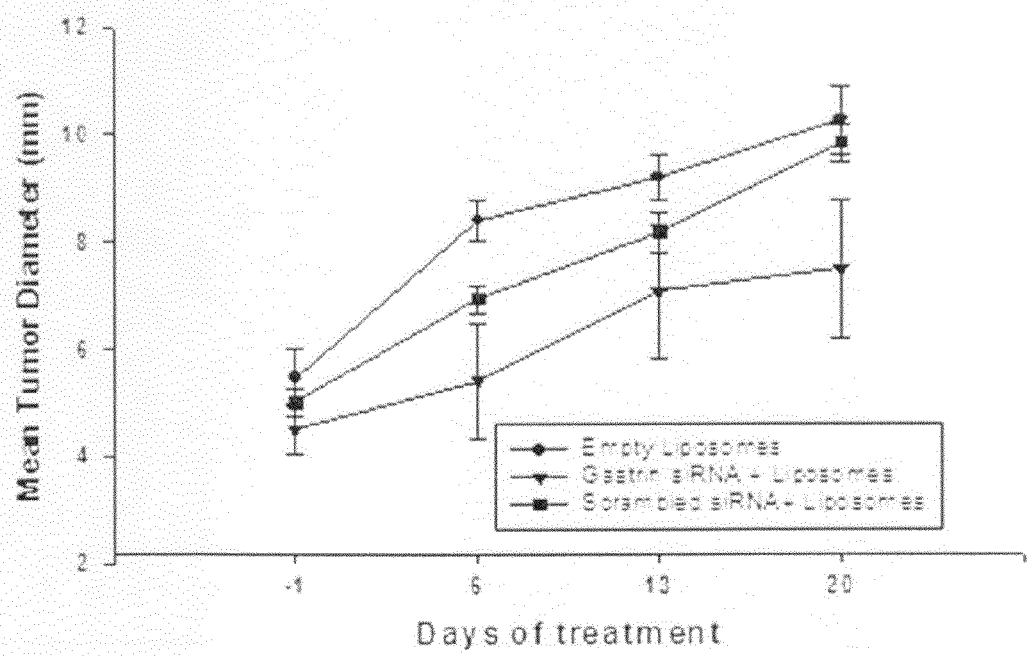

FIG. 7C. Weekly tumor diameters of AsPC-1 pancreatic tumor xenografts in mice treated with gastrin siRNA loaded nanoliposomes. After 3 weeks of treatment, mice treated with gastrin siRNA had tumors that were 25% smaller compared to mice treated with empty nanoliposomes or nanoliposomes loaded with scrambled siRNA controls ($p=0.07$).

FIG. 8A is a series of tables showing the composition of nanoliposomes at different level concentrations of PEG (2000)-DSPE.

Figure 8B:
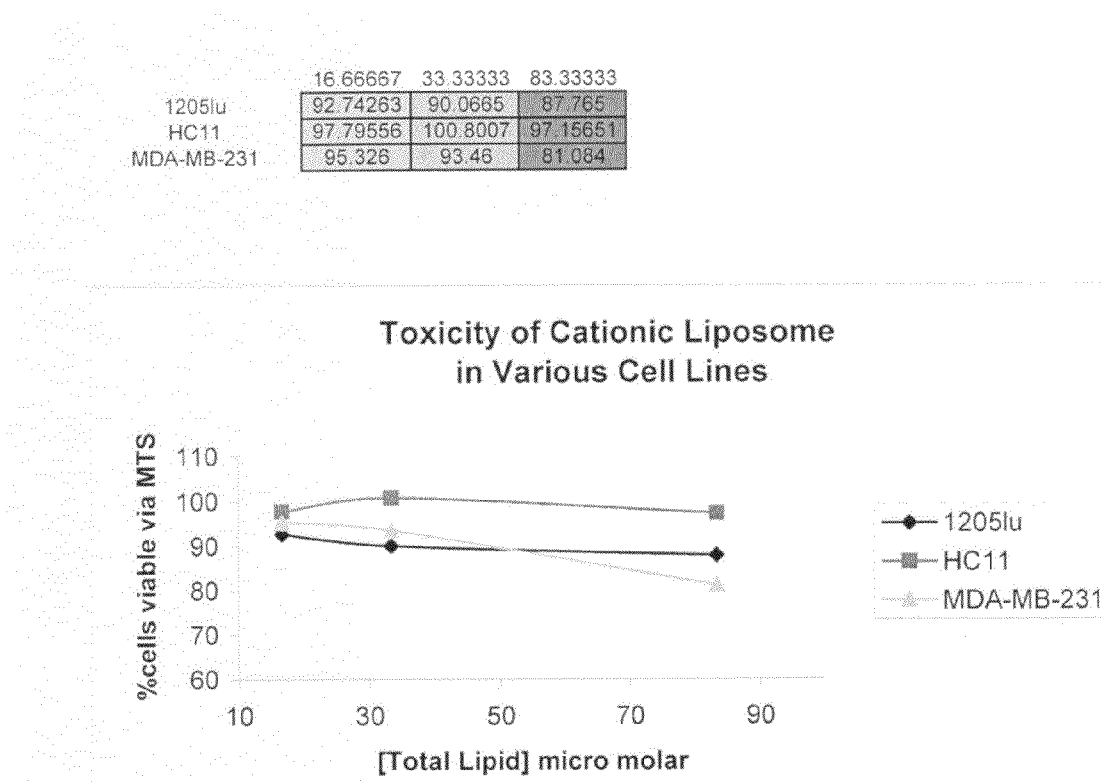

FIG. 8B shows a graph that indicates that the pegylated nanoliposomes of FIG. 8A, at 3.75%, are not cytotoxic to various cancer and non-cancer cell lines over a broad range of lipid concentrations.

Figure 9:
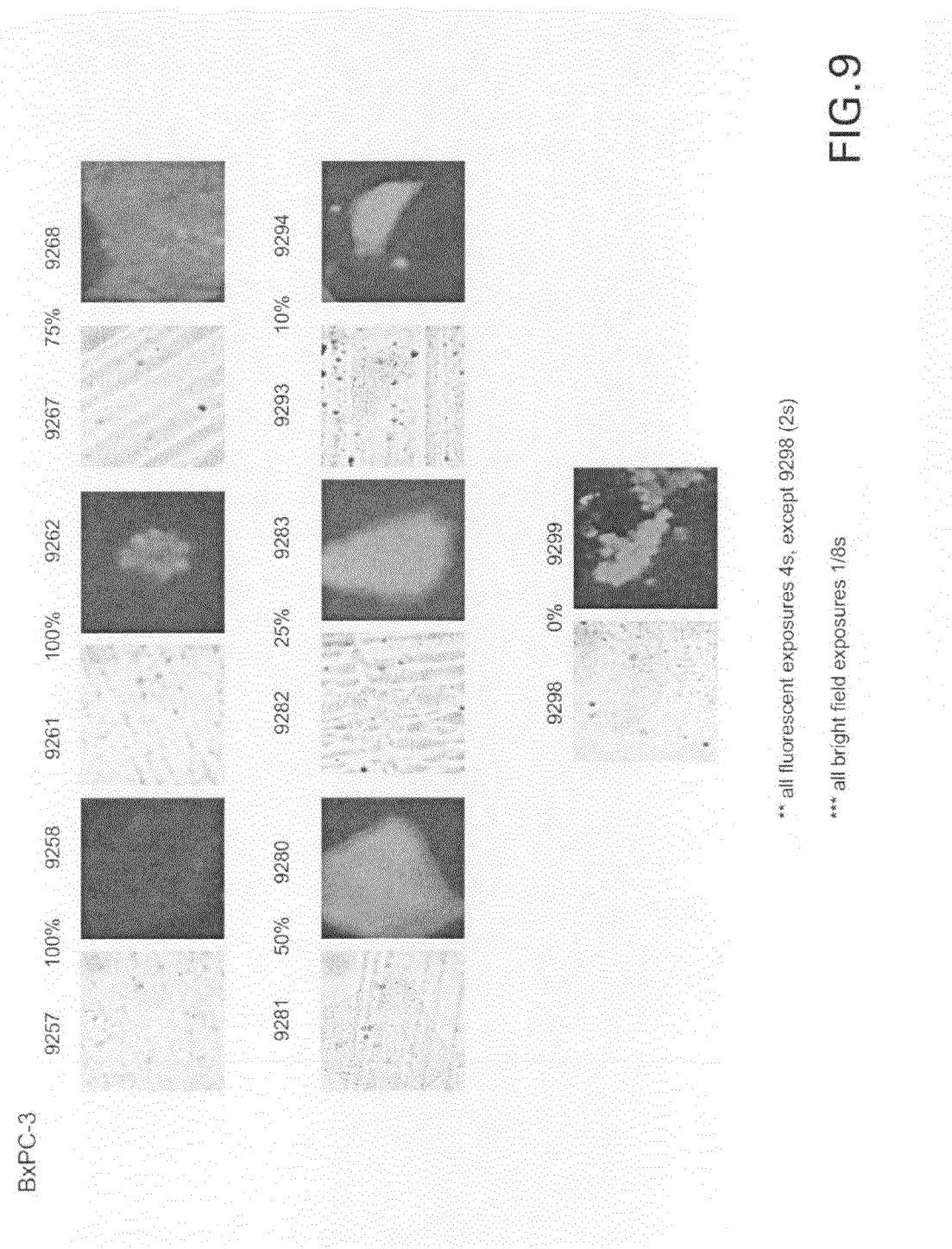

FIG. 9 shows the fluorescence and bright field images of pancreatic cancer cells BxPC-3 after exposure to nanoliposomes pegylated with different percentages of polyethylene glycol (PEG). At lower PEG concentrations, the images show more liposome incorporation.

Figure 10:
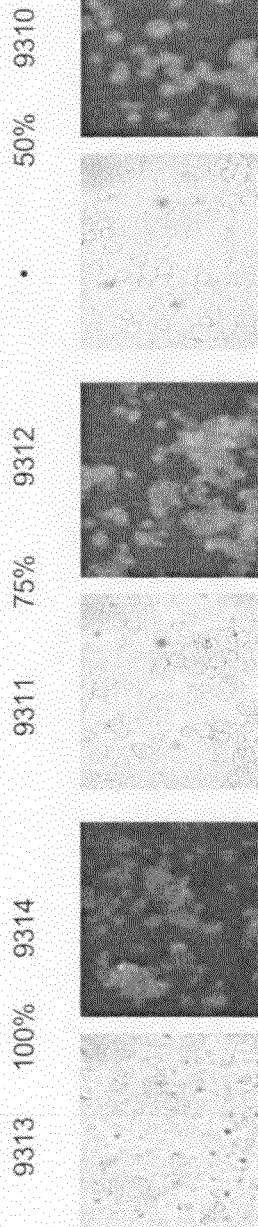

FIG. 10 shows the fluorescence and bright field images of pancreatic cancer cells AsPC-1-pLULIP c1.7 after exposure to nanoliposomes pegylated with different percentages of polyethylene glycol (PEG). At lower PEG concentrations, the images show more liposome incorporation.

DETAILED DESCRIPTION OF THE INVENTION

Gastrin has previously been demonstrated to stimulate growth of pancreatic cancer. It has been discovered that stable, long-term reduction in gastrin synthesis through RNA interference techniques significantly reduces pancreatic tumor growth in vivo. The parallel techniques of antisense and shRNA (a stable form of RNAi) transfection were employed to achieve lasting knockdown in gastrin mRNA and peptide levels. These methods permit the analysis of long-term gastrin knockdown on in vivo tumor formation and metastasis as well as a quantitative assessment of gastrin mRNA levels in clonal tumor cell populations. Novel RNAi target sites in the gastrin mRNA are described that effectively decrease gastrin expression in human pancreatic cancer cells and reduce orthotopic tumor growth in vivo. For the first time the use of cationic nanoliposomes as a vehicle for gastrin siRNAs to treat pancreatic tumors has been achieved. The details of the materials and methods employed are fully set forth in Appendix "A." The genomic data for the specification of the antisence and shRNA constructs is set forth in Appendix "B."

Figure 1A:
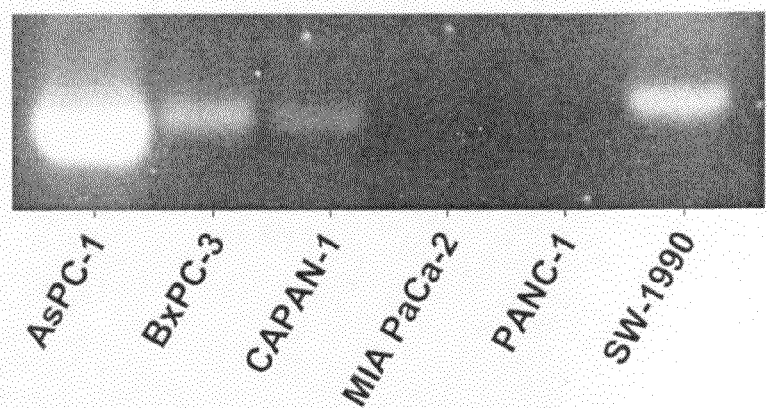
FIG. 1A. End-point RT-PCR
Figure 1B:
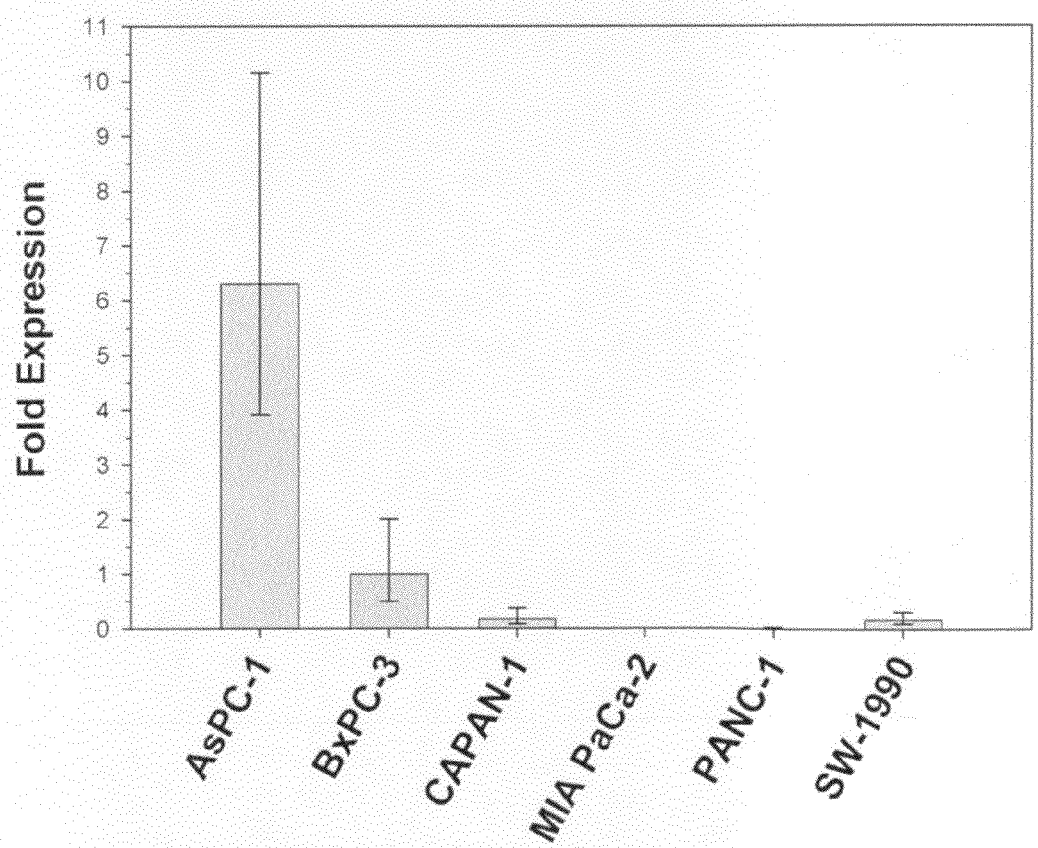
FIG. 1B. Real-Time RT-PCR analysis of gastrin mRNA levels in wild-type pancreatic cancer lines AsPC-1, BxPC-3, Capan-1, MIA PaCa-2, PANC-1 and SW-1990.
Figure 1C:
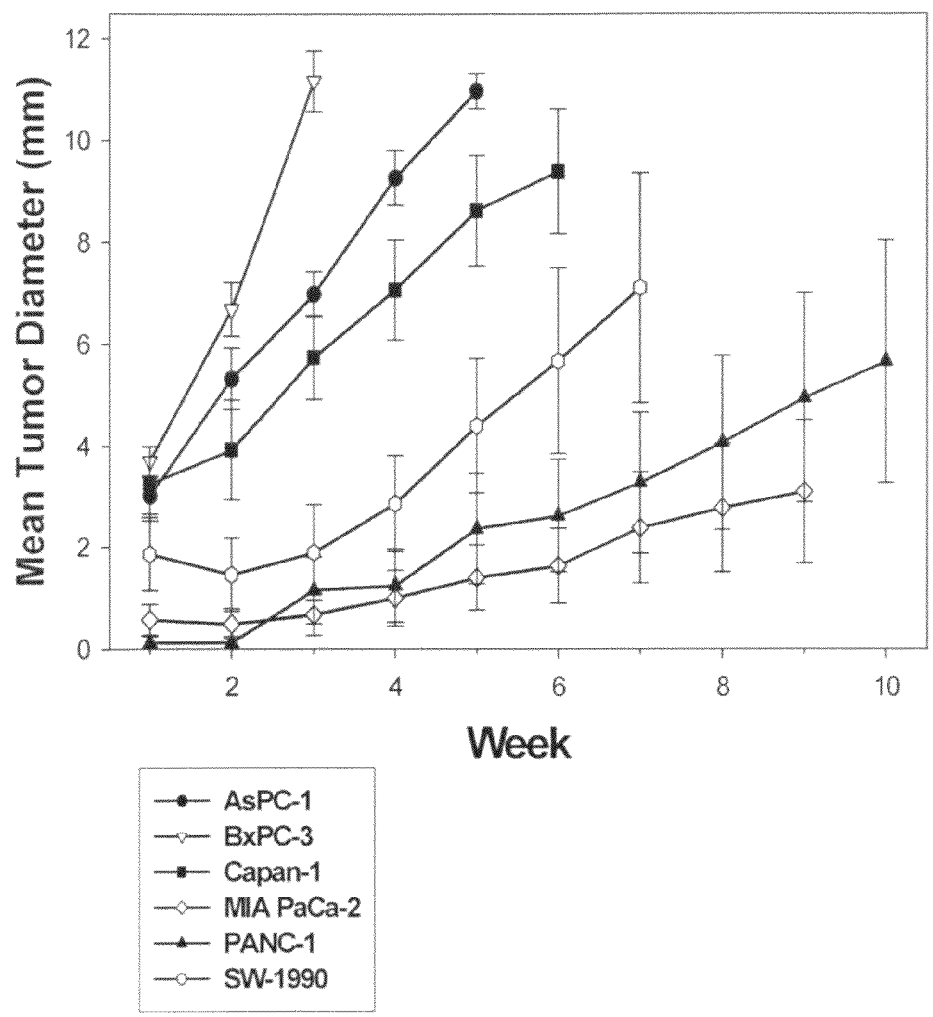
FIG. 1C. Subcutaneous tumor growth of human pancreatic cancer cells in nude mice corresponds to gastrin mRNA endogenous levels. Data points represent mean tumor diameter (mm)±SEM. Mice were necropsied if the mean tumor diameter reached 12 mm or at 10 weeks.

A. Gastrin mRNA, Tumor Growth, and Gastrin Peptide Expression of Wild-Type Cell Lines Six different human pancreatic cancer cell lines were tested for gastrin mRNA expression, tumor growth in vivo. End point RT-PCR (FIG. 1A) and Real-Time PCR (FIG. 1B) showed the detectable gastrin mRNA in all the cell lines. Gastrin mRNA levels were the highest in AsPC-1 cells and decreasing as follows: AsPC-1>BxPC-3>SW1990>Capan-1>MIA PaCa-2>PANC-1. The rate of subcutaneous xenografted tumor growth correlated with the gastrin mRNA expression (FIG. 1C) with BxPC-3 and AsPC-1 cells establishing 12-mm diameter tumors the fastest, in 2-4 weeks. Although the duration of tumor growth for PANC-1 and MIA PaCa-2 cells was extended to 8-10 weeks, these tumors never reached the size of the tumors containing higher concentrations of gastrin (FIG. 1C).

Figure 2:
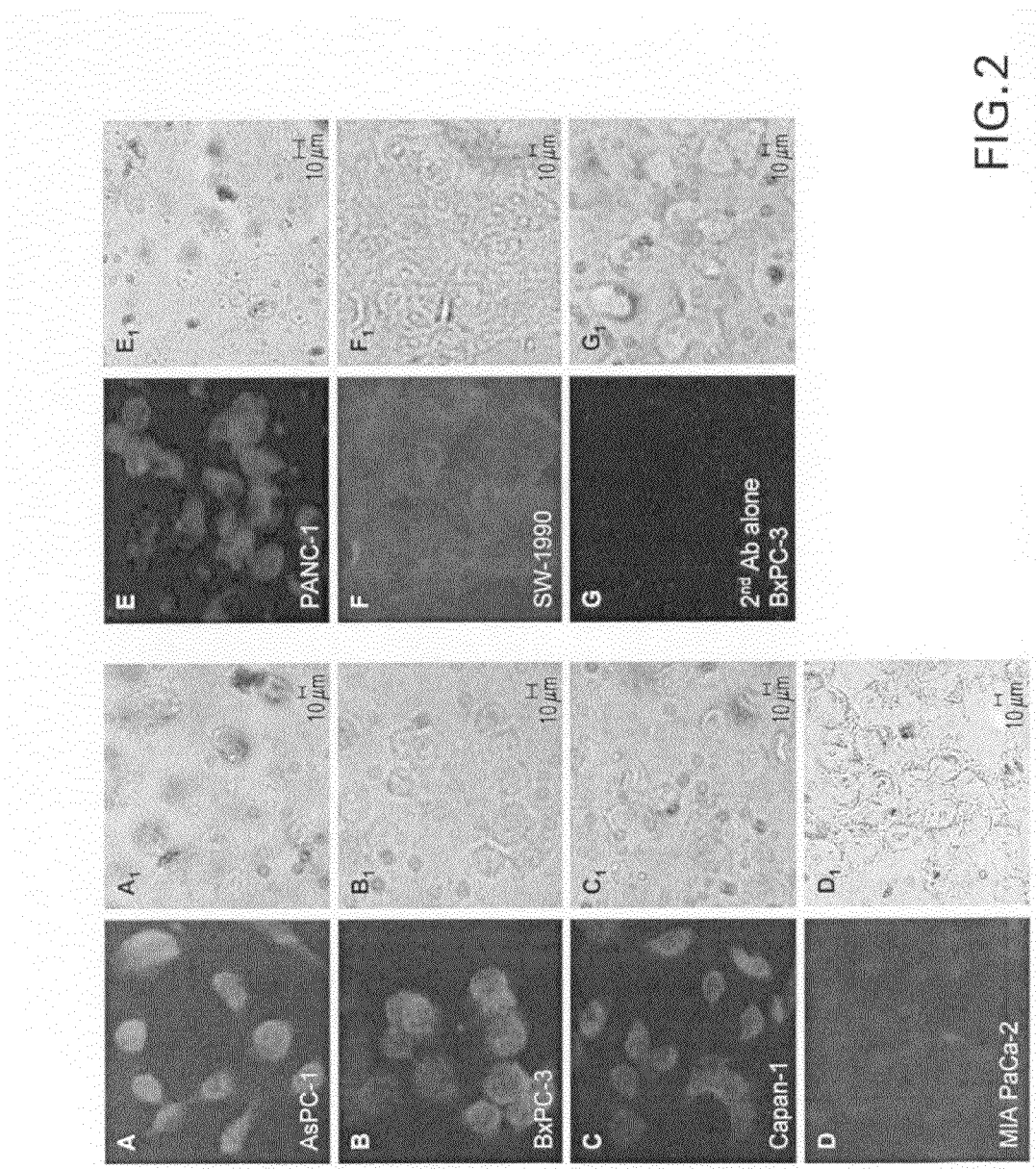
FIG. 2. Immunofluorescence analysis of gastrin peptide expression in wild-type human pancreatic cancer cells. Human cultured pancreatic cells were stained with anti-gastrin antibody (1:1,000) and secondary goat anti-rabbit rhodamine labeled antibody (1:2,000).

To evaluate whether gastrin peptide levels correlated with gastrin mRNA levels, gastrin immunoreactivity was also assessed in wild-type human pancreatic cancer cells. The amount of gastrin immunoreactivity was greatest in the cell lines expressing the largest quantities of gastrin mRNA (FIG. 2). AsPC-1 and BxPC-3 cells had the most gastrin staining (A and B) while gastrin immunofluoresence in MIA PaCa-2 and PANC-1 (D and E) was lower. Gastrin immunoreactivity was consistent with a plasma membrane and cytoplasmic location and was not nuclear. BxPC-3 cells reacted with secondary antibody only did not stain for gastrin peptide (FIG. 2, G), and Cos-1 kidney cells, an additional negative control, did not show gastrin immunoreactivity (data not shown).

B. Analysis of Endogenously Produced and Secreted Gastrin from Cancer Cells by HPLC and Mass Spectroscopy Lyophilized spent media from cultured pancreatic cancer cells (BxPC-3) was evaluated by HPLC and the gastrin peptide peak was collected and analyzed by mass spectroscopy. Mass spectroscopy confirmed the peak was gastrin-17. No glycine-extended gastrins or early precursor forms were indentified (data not shown).

C. Stable Expression of Gastrin Antisense or shRNAs Decreases the Levels of Gastrin mRNA Multiple BxPC-3 clones containing empty vector or gastrin antisense cDNA were established in cell culture. Stable knockdown of gastrin mRNA was confirmed by Real-Time RT-PCR (FIG. 3A). No difference in gastrin mRNA levels was identified between wild-type BxPC-3 cancer cells and empty vector transfected control clones—both produced high levels of gastrin mRNA. Antisense gastrin transfected clones varied in the extent of gastrin mRNA reduction: clones 13 and 24 had moderate gastrin mRNA expression with an average of 79% less gastrin mRNA than empty vector transfected control clones ($p<0.001$). In contrast, clones 67, 77 and 122 had very low gastrin mRNA with greater than 90% reduction when compared to vector controls (p<0.00005). The difference in gastrin mRNA levels between these groups (moderate-gastrin expressing clones 13 and 24 versus very low-gastrin expressing clones 67, 77 and 122) also was significant (p<0.000002) (FIG. 3A). Gastrin antisense clone 48 had no detectable gastrin mRNA.

To establish the efficacy of the gastrin shRNA constructs, gastrin mRNA was quantified in BxPC-3 cells that were stably transfected with a nonspecific shRNA or one of three shRNA constructs targeting independent regions of the gastrin mRNA. Two BxPC-3 clones for each gastrin shRNA target site (sh90, sh248 and sh286), as well as two nonspecific control clones, were selected for further analysis. Wild-type BxPC-3 cells and BxPC-3 clones stably transfected with the nonspecific shRNA had no differences in gastrin mRNA levels as determined by Real-Time RT-PCR (FIG. 3B). Regardless of the shRNA construct used, the gastrin shRNA knockdown clones all had a significant reduction in gastrin mRNA as compared to controls (p<0.01) (FIG. 3B). Gastrin sh90 and sh286 clones had an average of more than 90% reduction in gastrin mRNA levels, and one gastrin shRNA clone, sh90 clone 39, had no detectable gastrin mRNA.

D. Gastrin mRNA Down-Regulation Reduces Subcutaneous, In Vivo Tumor Growth

In addition to reduced gastrin mRNA levels, antisense gastrin and gastrin shRNA clones had significantly slower tumor growth in vivo. Subcutaneous growth rates for wild-type BxPC-3 cells and empty vector transfected controls were similar, both reaching a mean tumor diameter of 12 mm in less than 3 weeks (FIG. 4A). The moderate gastrin-producing BxPC-3 antisense clones 13 and 24 still developed tumors of equal size as wild-type and empty-vector transfected clones, but the lag-time to reach a 12 mm diameter tumor was increased from three to five weeks (FIG. 4A). Antisense clone 48, although greatly reduced in gastrin mRNA expression, grew similarly to clones 13 and 24. Most antisense gastrin clones with very low gastrin mRNA (67, 77 and 122) either failed to produce measurable tumors or had minimal growth of the subcutaneously injected tumor cells over a 10-week observation period.

Like the gastrin antisense clones, all of the gastrin shRNA clones formed smaller subcutaneous tumors than wild-type cells or nonspecific shRNA clones. At two weeks after injection, the mean tumor mass for gastrin shRNA clones was 83% less than for subcutaneous tumors from the nonspecific control clones (FIG. 4B, p<0.0003). The gastrin sh90 clones, which had the lowest level of gastrin mRNA, also formed the smallest subcutaneous tumors.

E. Orthotopic Tumor Growth and Metastasis in Gastrin Knockdown Clones

Because subcutaneous tumor formation may not completely replicate tumor growth in the pancreas and does not allow for the accurate study of metastasis, the effects of gastrin down-regulation were also assessed in an orthotopic model. Moderate gastrin expressing clones, with an average of 79% reduction in gastrin mRNA, developed orthotopic pancreatic tumors in nude mice that were similar in size to wild-type cells or empty vector clones (FIG. 5A). These clones generally formed comparable numbers of metastases as wild-type and empty-vector controls. However, antisense clone 48—which had very low gastrin mRNA levels—grew at a similar rate as the other moderate gastrin-producing clones but failed to metastasize (FIG. 5B). Antisense gastrin clones with >90% reduction in gastrin mRNA failed to produce an orthotopic tumor after 10 weeks. Overall, in animals where tumors did form, tumor mass and gastrin expression was correlated ($r=0.721$, $p=0.028$), and the number of metastases also correlated to gastrin mRNA levels ($r=0.737$, $p=0.024$).

Orthotopic pancreatic tumor mass was also significantly reduced in tumors formed by gastrin shRNA clones (FIG. 5C). No difference in tumor mass was found between tumors established with either wild-type BxPC-3 cancer cells or cells transfected with the nonspecific shRNA construct control. Tumors derived from clones of the three independent gastrin shRNA groups (sh90, sh248 and sh286) did not differ significantly in tumor mass from each other. Tumors from sh90 clones and sh286 clones weighed 98% and 84% less than the wild type and nonspecific control tumors, respectively. Tumors from sh248 clones were 63% smaller in mass than control tumors. Orthotopic tumor growth was significantly correlated with gastrin mRNA levels ($r=0.710$, $p=0.049$). The gastrin shRNA clone with undetectable gastrin mRNA expression (sh90 clone 39) failed to form orthotopic tumors (n=6 mice). In addition to a reduction in the size of the primary tumor in gastrin knockdown clones, the number of metastases from the orthotopic tumor site was significantly decreased for the sh90 and sh286 clones (FIG. 5D). Gastrin sh248 clones, however, formed metastases at a rate comparable to wild-type and nonspecific control clones (p=0.8).

F. Gastrin Peptide, Ki-67, and Cleaved Caspase-3 Expression are Affected by Gastrin mRNA Down-Regulation To confirm that reduced gastrin mRNA resulted in diminished gastrin peptide levels and that a reduction in orthotopic tumor mass was correlated with lowered gastrin peptide levels, immunofluorescence for gastrin peptide was performed on tumor sections. Wild-type BxPC-3 orthotopic tumors showed significant amounts of gastrin peptide expression, as determined by anti-gastrin antibody immunoreactivity (FIG. 6, A1). As expected, gastrin reactivity was localized to the cytoplasm/cell membrane and not in the nucleus. Gastrin immunofluorescence in tumor sections from BxPC-3 control transfectants, either empty vector (Vector, B1) or nonspecific shRNA (NSC, E1), was comparable to that in wild type tumors. Gastrin immunoreactivity was markedly decreased in tumor sections from all three gastrin shRNA clones (F1, G1, and H1). In tumor sections from antisense clones with moderate amounts of gastrin mRNA, gastrin staining was only slightly decreased (C1 and D1). Because no tumors developed in the antisense transfected cells with a >90% reduction in gastrin mRNA, gastrin immunoreactivity could not be assessed. No background immunofluoresence was detected in BxPC-3 wild type tumor sections reacted with their respective polyclonal or monoclonal secondary antibody alone (I1-I3). Bright field controls (J1-J3) are also shown.

Because gastrin signaling in tumor cells increases proliferation and decreases apoptosis, orthotopic tumor sections were also evaluated for the proliferation marker, Ki-67, and the apoptosis marker, cleaved caspase-3. Ki-67 immunoreactivity was marked in the nucleus of the wild type (FIG. 6, A2) and control tissues (FIG. 6, B2 & E2) and directly corresponded to the amount of gastrin produced by a particular tumor. Ki-67 staining in the moderate gastrin expressing antisense clones was not significantly decreased (C2 and D2), consistent with the ability of these clones to form larger tumors. In contrast, gastrin shRNA clones with low gastrin expression and small tumor mass also exhibited a faint reaction for Ki-67 (F2, G2, and H2). Thus there is a positive correlation between gastrin and the Ki-67 proliferation marker.

The apoptosis marker, cleaved caspase-3, inversely corresponded to gastrin peptide levels. Cleaved caspase-3 immunoreactivity was barely detectable in wild type and control cells (FIG. 6, A3, B3 and E3). However, cleaved caspase-3 immunoreactivity was apparent in the cytoplasm of all the gastrin shRNA clones (F3, G3, and H3). Again the moderate gastrin antisense clones, which formed large orthotopic tumors, had less cleaved caspase-3 staining (C3 and D3). Gastrin peptide levels were negatively correlated to cleaved caspase-3 reactivity. Overall, the smaller tumor size of BxPC-3 clones expressing the gastrin shRNAs can be attributed both to decreased proliferation and increased apoptosis of the tumor cells.

G. Gastrin siRNA Laden Cationic Nanoliposomes Decrease Gastrin mRNA and Inhibit Pancreatic Tumor Growth in Mice Since it has now been demonstrated that gastrin shRNA286 effectively inhibits gastrin mRNA expression and impairs tumor growth in stably transfected BxPC-3 cells, the ability of an siRNA directed against the same gastrin mRNA sequence to reduce gastrin mRNA expression in vitro and decrease growth of established pancreatic tumor xenografts in vivo was tested and experimentally verified for the first time. Because the half-life of siRNAs in the peripheral blood is short, cationic nanoliposomes were employed as a delivery vehicle to administer the gastrin siRNA or scrambled control siRNA. The ability of the siRNAs packaged in nanoliposomes to reduce gastrin mRNA expression was tested in vitro with BxPC-3 cancer cells. After 72 hrs of treatment with gastrin siRNA loaded nanoliposomes or with scrambled gastrin siRNA loaded nanoliposomes, knockdown of gastrin mRNA was observed in the gastrin siRNA treated cells compared to untreated cells (p<0.001) (FIG. 7A). Since the decrease in gastrin mRNA with the siRNA/nanoliposome treatment was not as dramatic as with the gastrin shRNA, addition tests were done to determine if different pancreatic cancer cell lines took up nanoliposomes equally. Uptake of fluorescently labeled nanoliposomes by a variety of pancreatic cell lines was compared to assess which cells took up the nanoliposomes most efficiently. AsPC-1 cells demonstrated the highest levels of nanoliposome uptake (FIG. 7B). Therefore, AsPC-1 cells were used for further testing of gastrin siRNAs loaded into nanoliposomes in an in vivo tumor model. Mice bearing subcutaneous AsPC-1 tumor xenografts were treated by tail vein injection with gastrin siRNA in nanoliposomes, the corresponding scrambled gastrin siRNA in nanoliposomes, or with empty nanoliposomes every other day for 3 weeks. Mice treated with empty nanoliposomes or nanoliposomes containing the scrambled gastrin siRNA had tumors that grew at a similar rate. However mice treated with nanoliposomes containing gastrin siRNA formed tumors that were 25% smaller in size than the tumors in mice treated with either empty nanoliposomes or nanoliposomes loaded with scrambled siRNA (FIG. 7C).

Although it had previously been shown by ourselves[14,17] and others[32,35] that the gastrointestinal peptide gastrin plays a role in autocrine growth of pancreatic cancer, this patent application discloses for the first time the discovery that the amount of gastrin produced is directly correlated with the rate of tumor growth and the development of metastases. Endogenous levels of gastrin mRNA and peptide in untransfected, wild type pancreatic cancer cell lines paralleled their rate of tumor growth in vivo. The demonstration that gastrin production varies in different cultured pancreatic cancer cell lines may account for the variation in tumor growth rates reported by many investigators. Obviously other factors are involved, since among the cell lines examined the ascites-derived pancreatic cancer cell line AsPC-1 made the most gastrin but grows slightly slower than BxPC-3 (which makes the second greatest quantity of gastrin). Therefore, to test the effects of anti-gastrin constructs on pancreatic tumor growth in vivo, the most aggressive cell line, BxPC-3 was utilized. Among BxPC-3 clones transfected with antisense gastrin, a variety of levels of gastrin expression were observed. Tumor growth rate was positively correlated with the quantity of gastrin mRNA and gastrin peptide produced by each clone. Likewise, the effects of antisense-based gastrin reduction on proliferation and apoptosis—both known to be affected by gastrin signaling—were also directly correlated to the level of gastrin mRNA and peptide.

Significantly, it has been discovered that there is a threshold of gastrin mRNA suppression necessary in order to eliminate pancreatic tumor growth in vivo. The gastrin antisense clones that had a 79% suppression of gastrin mRNA expression still formed tumors, whereas those clones with 90% or more reduction in gastrin mRNA failed to form tumors. Where gastrin expression was only moderately decreased (antisense clones 13 and 24), Ki-67 and cleaved caspase-3 levels also were essentially unchanged. A similar effect was seen with gastrin knockdown clones derived with RNAi techniques. Gastrin shRNA clones with a reduction in gastrin mRNA of >90% formed significantly smaller tumors, with reduced Ki-67 staining and increased cleaved caspase-3 staining. In the gastrin shRNA clones with a >99% reduction in gastrin mRNA tumor formation was completely blocked. This suggests that pancreatic cancer cells produce much more gastrin than is required for autocrine-stimulated growth. Thus, significant knockdown of gastrin mRNA levels must occur before an inhibition of tumor formation or reduction in tumor size can be seen.

Antisense gene targeting is a method used to frequently evaluate functional importance of cancer-related peptides in the laboratory; however, this method cannot be applied to human clinical trials. In contrast, RNA interference using siRNA has the potential of being applied not only to laboratory animals[36,37] but also in the treatment of patients with gastrointestinal malignancies[38]. Effective siRNA delivery techniques using nanotechnology are being developed[39] and targeting strategies are improving[40]. Previous work had demonstrated that gastrin siRNAs transiently expressed in pancreatic cancer cells slowed growth, however this study was only done in vitro[32]. Although one of the gastrin shRNA target sites that was employed, sh248, overlaps with a published gastrin siRNA target sequence[32], the most effective gastrin targeting sites have now been identified as sh90 and sh286, sites that were previously untested. In fact, the sh248 clones disclosed in this patent document formed larger orthotopic tumors than did sh90 or sh286 clones and did not have a reduction in the number of metastases. Our data indicate that the sh248 target site is less effective in reducing tumor growth and metastasis, which was not evident in previous in vitro studies. These results clearly demonstrate that the gastrin shRNAs employed in this study effectively reduced tumor growth in vivo. In addition, we have discovered and verified the extent of gastrin knockdown required to impede in vivo tumor growth, not just suppress growth of tumor cells in culture. As may be expected, significantly reducing tumor growth in vivo with gastrin shRNA also prevented the formation of metastases, a frequent and serious complication of pancreatic cancer.

The characteristics of the gastrin shRNA knockdown tumors (decreased amounts of Ki-67 and increased levels of cleaved caspase-3) are consistent with the known effects of gastrin on cancer cell proliferation and apoptosis. The extent of gastrin mRNA knockdown in the various antisense and shRNA clones directly paralleled Ki-67 expression (i.e. high gastrin mRNA producing clones had high Ki-67 staining) and inversely tracked with cleaved caspase-3 expression (i.e. low gastrin mRNA producing clones had high cleaved caspase-3 staining). These findings suggest that the gastrin shRNAs used herein specifically target gastrin mRNA and that the reduction in tumor growth in gastrin shRNA clones was not due to off-target effects or clonal variation. The increase in cleaved caspase-3 and decrease in Ki-67 in gastrin shRNA clones demonstrates that reducing gastrin mRNA expression influences both anti-apoptotic and pro-proliferative pathways.

H. Optimization of Cationic Nanoliposomes as Delivery Vehicles for Gastrin siRNA In order to use RNAi therapy for the treatment of human subjects in the future, a delivery vehicle must be used to carry the RNAi agents to the target of choice. Since free siRNAs are rapidly degraded in the peripheral blood by nucleases, the delivery vehicle must provide a means to protect the siRNAs. Akter and Benter[39] recently reviewed the obstacles that must be overcome when designing delivery strategies for siRNAs in vivo. Stover and Kester[41] have shown that nanoliposomes can be an effective carrier vehicle for treating solid human tumors, such as breast cancer, in mice. Although the nanoliposomes disclosed in this patent document were not designed to be "end-organ target-specific" (i.e., reaching only pancreatic cancer cells and not other cells in the tumor bearing mouse), a 25% reduction in tumor size compare to both empty nanoliposome controls and nanoliposomes loaded with a scrambled siRNA control is observed. In addition to end-organ target-specific liposomes, further protecting the nanoliposomes from nuclease destruction in the peripheral blood should increase the concentration of RNAi agents delivered to the target. Pegylation of liposomes should further protect them. For pancreatic cancer cells it has been discovered that not all pegylation concentrations are optimal for nanoliposome uptake. FIG. 8A shows tables of different formulations of nanoliposomes as a function PEG(2000) concentration. FIG. 8B shows that with varing concentrations of total lipid (5, 10, 25 µM) using the 3.75% PEG formulation, there is no cellular toxicity in various cancer and non-cancerous cell lines. FIGS. 9 and 10 show that varying the amount of pegylation of the nanoliposomes affects their uptake by the two pancreatic cancer cell lines. Visually, one can observe by the increased flouresence that different percentage levels of pegylation result in different degrees of uptake. It can be seen that the greatest uptake occurs at a concentration of 3.75%. It has been clearly shown that there is an optimal PEG concentration for nanoliposomal uptake in gastrin expressing pancreatic cancer cells. It is expected that in vivo tumor reduction will increase using these PEG protected nanoliposomes.

Future studies with cancer-specific targeting of nanoliposomes will most likely impair tumor growth more effectively. However, our finding that there was a decrease in size of an established tumor offers potential promise for further exploring this means of therapy for human subjects with advanced pancreatic cancer. In addition, the use of a second cell line for these experiments (AsPC-1) demonstrates the effect of gastrin RNAi is not cell line specific.

All of these factors strongly indicate that gastrin is an attractive target for anti-cancer RNAi treatments. We have identified new and more effective RNAi target sequences in the human gastrin mRNA and have demonstrated the efficacy of using anti-gastrin RNAi based technologies to inhibit tumor growth and metastasis in vivo. This information can be applied to the development of new therapeutic agents for gastrointestinal malignancies. RNAi targeting of gastrin, which is vital to pancreatic cancer cells, may provide a novel approach to treating this disease.

REFERENCES

1. Dembinski A B, Johnson L R. Stimulation of pancreatic growth by secretin, caerulein, and pentagastrin. *Endocrinology*. 1980; 106:323-328.
2. Johnson L R, McCormack S A. Regulation of gastrointestinal mucosal growth. In: Johnson L R, ed. *Physiology of the gastrointestinal tract*. 3rd ed. New York: Raven Press, 1994:611-642.
3. Singh P, Walker J P, Townsend C M, Jr., et al. Role of gastrin and gastrin receptors on the growth of a transplantable mouse colon carcinoma (MC-26) in BALB/c mice. *Cancer Res*. 1986; 46:1612-1616.
4. Smith J P, Solomon T E. Effects of gastrin, proglumide, and somatostatin on growth of human colon cancer. *Gastroenterology*. 1988; 95:1541-1548.
5. Smith J P, Stock E A, Wotring M G, et al. Characterization of the CCK-B/gastrin-like receptor in human colon cancer. *Am J Physiol*. 1996; 271:R797-R805.
6. Upp J R, Jr., Singh P, Townsend C M, Jr., et al. Clinical significance of gastrin receptors in human colon cancers. *Cancer Res*. 1989; 49:488-492.
7. Smith J P, Shih A H, Wotring M G, et al. Characterization of CCK-B/gastrin-like receptors in human gastric carcinoma. *Int J Oncol*. 1998; 12:411-419.
8. Watson S, Durrant L, Morris D. Gastrin: growth enhancing effects on human gastric and colonic tumor cells. *Br J Cancer*. 1989; 59:554-558.
9. Rehfeld J F, Bardram L, Hilsted L. Gastrin in human bronchogenic carcinomas: constant expression but variable processing of progastrin. *Cancer Res*. 1989; 49:2840-2843.
10. Smith J P, Kramer S T, Solomon T E. CCK stimulates growth of six human pancreatic cancer cell lines in serum-free medium. *Regul Pept*. 1991; 32:341-349.
11. Smith J P, Solomon T E, Bagheri S, et al. Cholecystokinin stimulates growth of human pancreatic adenocarcinoma SW-1990. *Dig Dis Sci*. 1990; 35:1377-1384.
12. Smith J P, Fantaskey A P, Liu G, et al. Identification of gastrin as a growth peptide in human pancreatic cancer. *Am J Physiol*. 1995; 268:R135-R141.
13. Brand S J, Fuller P J. Differential gastrin gene expression in rat gastrointestinal tract and pancreas during neonatal development. *J Biol Chem*. 1988; 263:5341-5347.
14. Smith J P, Shih A, Wu Y, et al. Gastrin regulates growth of human pancreatic cancer in a tonic and autocrine fashion. *Am J Physiol*. 1996; 270:R1078-R1084.
15. Smith J P, Verderame M F, Zagon I S. Antisense oligonucleotides to gastrin inhibit growth of human pancreatic cancer. *Cancer Lett*. 1999; 135:107-112.
16. Smith J P, Hamory M W, Verderame M F, et al. Quantitative analysis of gastrin mRNA and peptide in normal and cancerous human pancreas. *Int J Mol Med*. 1998; 2:309-315.
17. Smith J P, Verderame M F, Ballard E N, et al. Functional significance of gastrin gene expression in human cancer cells. *Regul Pept*. 2004; 117:167-173.
18. Ferrand A, Wang T C. Gastrin and cancer: a review. *Cancer Lett*. 2006; 238:15-29.
19. Miyazaki Y, Shinomura Y, Tsutsui S, et al. Gastrin induces heparin-binding epidermal growth factor-like growth factor in rat gastric epithelial cells transfected with gastrin receptor. *Gastroenterology*. 1999; 116:78-89.
20. Varro A, Noble P J, Wroblewski L E, et al. Gastrin-cholecystokinin (B) receptor expression in AGS cells is associated with direct inhibition and indirect stimulation of 21. Fukui H, Kinoshita Y, Maekawa T, et al. Regenerating gene protein may mediate gastric mucosal proliferation induced by hypergastrinemia in rats. *Gastroenterology.* 1998; 115:1483-1493.
22. Guo Y S, Cheng J Z, Jin G F, et al. Gastrin stimulates cyclooxygenase-2 expression in intestinal epithelial cells through multiple signaling pathways. Evidence for involvement of ERK5 kinase and trans activation of the epidermal growth factor receptor. *J Biol Chem.* 2002; 277: 48755-48763.
23. Lei S, Dubeykovskiy A, Chakladar A, et al. The Murine Gastrin Promoter Is Synergistically Activated by Transforming Growth Factor-{beta}/Smad and Wnt Signaling Pathways. *J Biol Chem.* 2004; 279:42492-42502.
24. Stepan V, Ramamoorthy S, Pausawasdi N, et al. Role of small GTP binding proteins in the growth-promoting and antiapoptotic actions of gastrin. *Am J Physiol Gastrointest Liver Physiol.* 2004; 287:G715-G725.
25. Tomkova K, El Rifai W, Vilgelm A, et al. The gastrin gene promoter is regulated by p73 isoforms in tumor cells. *Oncogene.* 2006; 25:6032-6036.
26. Rengifo-Cam W, Umar S, Sarkar S, et al. Antiapoptotic effects of progastrin on pancreatic cancer cells are mediated by sustained activation of nuclear factor-{kappa}B. *Cancer Res.* 2007; 67:7266-7274.
27. Clarke P A, Dickson J H, Harris J C, et al. Gastrin enhances the angiogenic potential of endothelial cells via modulation of heparin-binding epidermal-like growth factor. *Cancer Res.* 2006; 66:3504-3512.
28. Brett B T, Smith S C, Bouvier C V, et al. Phase II study of anti-gastrin-17 antibodies, raised to G17DT, in advanced pancreatic cancer. *J Clin Oncol.* 2002; 20:4225-4231.
29. Chau I, Cunningham D, Russell C, et al. Gastrazole (JB95008), a novel CCK2/gastrin receptor antagonist, in the treatment of advanced pancreatic cancer: results from two randomised controlled trials. *Br J Cancer.* 2006; 94:1107-1115.
30. Grabowska A M, Morris T M, McKenzie A J, et al. Pre-clinical evaluation of a new orally-active CCK-2R antagonist, Z-360, in gastrointestinal cancer models. *Regul Pept.* 2008; 146:46-57.
31. Harris J C, Gilliam A D, McKenzie A J, et al. The biological and therapeutic importance of gastrin gene expression in pancreatic adenocarcinomas. *Cancer Res.* 2004; 64:5624-5631.
32. Grabowska A M, Hughes J, Watson S A. Use of interfering RNA to investigate the role of endogenous gastrin in the survival of gastrointestinal cancer cells. *Br J Cancer.* 2007; 96:464-473.
33. Tan M H, Nowak N J, Loor R, et al. Characterization of a new primary human pancreatic tumor line. *Cancer Invest.* 1986; 4:15-23.
34. Brown D C, Gatter K C. Monoclonal antibody Ki-67: its use in histopathology. *Histopathology.* 1990; 17:489-503.
35. Goetze J P, Nielsen F C, Burcharth F, et al. Closing the gastrin loop in pancreatic carcinoma: coexpression of gastrin and its receptor in solid human pancreatic adenocarcinoma. *Cancer.* 2000; 88:2487-2494.
36. Duxbury M S, Ito H, Zinner M J, et al. EphA2: a determinant of malignant cellular behavior and a potential therapeutic target in pancreatic adenocarcinoma. *Oncogene.* 2004; 23:1448-1456.
37. Wang Y, Zhu H, Quan L, et al. Downregulation of survivin by RNAi inhibits the growth of esophageal carcinoma cells. *Cancer Biol Ther.* 2005; 4:974-978.
38. Sklan E H, Glenn J S. The Power of silence: application of small interfering RNAs to gastrointestinal diseases. *Gastroenterology.* 2007; 132:2291-2295.
39. Akhtar S, Benter I F. Nonviral delivery of synthetic siRNAs in vivo. *J Clin Invest.* 2007; 117:3623-3632.
40. Szoka F. Molecular biology. The art of assembly. *Science.* 2008; 319:578-579.
41. Stover T C, Sharma A, Robertson G P, et al. Systemic delivery of liposomal short-chain ceramide limits solid tumor growth in murine models of breast adenocarcinoma. *Clin Cancer Res.* 2005; 11:3465-3474.

APPENDIX "A"

Materials and Methods

Cell Lines and Cultures

BxPC-3 human pancreatic cancer cells, established in culture by Tan et al.[33], are a moderately-differentiated pancreatic cancer cell line. BxPC-3 produces fully processed gastrin, which stimulates growth in an autocrine fashion[14]. All cell lines used in the experiments were purchased from the ATCC (Rockville, Md.), and were maintained in the appropriate media (DMEM with 10% FBS for PANC-1, MIA PaCa-2 and SW1990; Iscove's with 20% FBS for Capan-1; and RPMI 1640 with 10% FBS for BxPC-3 and AsPC-1).

Gastrin Antisense or shRNA Constructs and BxPC-3 Transfection

A full-length human gastrin antisense cDNA in the vector pcDNA3.1 (Invitrogen, Carlsbad, Calif.) was transfected into BxPC-3 human pancreatic cancer cells using Lipofectamine-2000 (Invitrogen). Control cells were transfected with an empty vector. BxPC-3 cells were also independently transfected with one of three shRNA constructs (short hairpin RNAs) targeting different regions of gastrin mRNA. Selection of shRNA sites was based upon the gastrin mRNA secondary structure, as determined by the m-fold program, and low off-target effects. The shRNAs used herein started at bases +90, +248 and +286 and sequences were as follows: sh90—GAUGCACCCUUAGGUACAG (SEQ ID NO: 1); sh248—AGAAGAAGCCUAUGGA-UGG (SEQ ID NO: 2); and sh286—GUGCUGAGGAUGAGAACUA (SEQ ID NO: 3). Nonspecific shRNA controls (NSC) contained an shRNA oligonucleotide duplex with no known homology to any mammalian gene sequence (Oligoengine, Seattle, Wash.). All shRNA duplexes were cloned into the pSuper.neo vector and verified by DNA sequence analysis. BxPC-3 clones that stably incorporated the vector controls, gastrin antisense constructs, or gastrin shRNA constructs were identified by G418 resistance and confirmed by RT-PCR (below).

Measurement of Gastrin mRNA by RT-PCR

Gastrin end-point RT-PCR was used to screen and select antisense and shRNA transfected BxPC-3 clones with reduced gastrin mRNA levels. RNA was extracted using Trizol (Invitrogen) or RNeasy (Qiagen, Valencia, Calif.). Total RNA (0.5 µg each) was subjected to DNase digestion for 30 min at 37° C., followed by 5 min at 95° C. End-point RT-PCR was performed using a One Step/Superscript III kit (Invitrogen). The PCR primers were designed to span an intron so that any PCR products generated from residual genomic DNA could be differentiated from PCR products arising from gastrin mRNA. Human gastrin primer sequences were as follows: gastrin forward 5'-CAGCGACTATGTGTGTATGT-GCTG-3' (SEQ ID NO: 4), gastrin reverse 5'-GAAGTCCATCCATCCATAGGC-3' (SEQ ID NO: 5).

The PCR products were analyzed in a 1.5% agarose gel and bands were quantified using an Eagle Eye imaging system (Stratagene, La Jolla, Calif.).

Real-Time RT-PCR was also used to quantify gastrin mRNA in wild-type pancreatic cancer cells and in transfected BxPC-3 clones. RNA (18S and 28S bands) was quantified using the Agilent 2100 Bioanalyzer (Agilent Technologies). First strand cDNA was produced from 1.0 µg of total RNA using random hexamer primers and a SuperScript III Reverse Transcription kit (Invitrogen). The concentration and quality of resulting cDNA was quantified using the Agilent 2100 Bioanalyzer or the NanoDrop ND-1000 (NanoDrop Technologies, Wilmington, Del.). Samples were standardized to 30 ng/µl, and 60 ng of cDNA per reaction was analyzed using a human gastrin ABI Taqman kit with 18S ribosomal RNA as the internal control. To exclude the possibility of genomic DNA contamination, control reactions with no cDNA template were performed. PCR amplification and analysis were done with the Applied Biosystems Sequence Detection System 7300 using the Relative Quantification (ddCt) Plate setup. At least four replicates were performed.

Analysis of Endogenously Produced and Secreted Gastrin from Cancer Cells by HPLC and Mass Spectroscopy Conditioned media from log-phase BxPC-3 human pancreatic cancer cells was analyzed by HPLC to determine whether the cells endogenously secrete gastrin analogues. Media samples from BxPC-3 cells grown for 24, 48 or 72 hours in serum-free media (n=6 samples/day) were lyophilized and redissolved in $NH_4CO_4$. Samples were run on a C18 reverse phase HPLC column on a Beckman System Gold with an acetonitrile gradient of 25-40%. Fractions were collected every 30 sec from time 37.0 min until time 42.0 min to collect the gastrin fraction, which elutes at 39.8 min. Fractions were stored at −80° C. and further analyzed by mass spectrometry.

In Vivo Tumor Growth of shRNA Selected Clones

Athymic nude mice (Harlan, 6-week old male nu/nu) were used for all in vivo tumor growth experiments. The research protocol was approved by the Institutional Animal Care and Usage Committee of the Pennsylvania State University College of Medicine and animals were housed in accordance with the AAACCR guidelines for veterinary medicine. Subcutaneous tumors were established by injecting $10^6$ cells in 0.1 ml into the right and left flanks. Orthogonal tumor measurements [Formula=√(l×w)] were done weekly and tumors were removed when the mean tumor diameter was 12 mm.

For orthotopic tumors, mice were fully anesthetized with a mixture of ketamine-HCl (129 mg/kg) and xylazine (4 mg/kg) intramuscularly. A small incision was made in the left flank, peritoneum dissected and pancreas exposed. Cells ($10^6$ cells in 0.1 ml) were injected into the pancreas using a 27-gauge needle. The incision was closed with sterile staples and allowed to heal for 7 days prior to staple removal. At least 6 animals were analyzed for wild-type cells and for each clone (vector controls, gastrin antisense, gastrin shRNAs or nonspecific shRNA controls).

Animals were necropsied at 5-weeks following tumor cell injection for wild type, vector only, and nonspecific shRNA controls and up to 10-weeks post-injection for gastrin antisense or gastrin shRNA clones for all orthotopic experiments and for the subcutaneous antisense clones. Animals were necropsied at 2 weeks for the subcutaneous shRNA clones. Visible metastatic lesions were evaluated in the orthotopic model throughout the thoracic and peritoneal cavities including the lymphatics, lung, liver, intestine, and spleen.

Immunofluorescence Detection of Gastrin Peptide, Ki-67, and Cleaved Caspase-3

Gastrin Immunoreactivity:

Wild-type human pancreatic cancer cells were plated onto 22 $mm^2$ round glass coverslips and grown in appropriate media for 36-48 hrs (log phase). The media was removed, cells washed, and fixed with ice-cold methanol and acetone for 10 minutes each. Nonspecific binding was blocked with Sorenson's Phosphate Buffer (SPB) containing 3% FBS and 0.1% Triton-X-100 for 1 hour. Cells were subsequently incubated in the same buffer containing a rabbit polyclonal gastrin antibody (T-4347, Peninsula Labs, Carlsbad, Calif.) at a titer of 1:1,000 overnight (18 hours) at 4° C. After three washes in SPB containing 1% FBS, the cells were incubated in SPB containing 3% FBS, 0.1% Triton-X-100 and the secondary goat anti-rabbit rhodamine-labeled antibody (1:2,000) (Amersham Biosciences, Piscataway, N.J.) for 2 hours at 4° C. in the dark. The slides were washed twice with SPB for 30 minutes each and mounted with Aqua Poly/Mount solution (Polysciences, Warrington, Pa.). Controls included Cos-1 monkey kidney cells and wild-type BxPC-3 cells incubated with secondary antibody alone. Flash frozen orthotopic tumors were mounted in OCT compound (Sukura, Torrance, Calif.) and sectioned (12 µm). Tissue sections were treated as above but with a primary antibody titer of 1:200 and a secondary antibody titer of 1:1,000. The tissues were visualized for gastrin immunoreactivity by fluorescence microscopy.

Ki-67 Immunoreactivity:

Tissue sections were reacted with a mouse monoclonal antibody to Ki-67 to assess cellular proliferation[34]. Detection of Ki-67 was carried out using Mouse on Mouse (M.O.M.) kit from Vector Laboratories (Burlingame, Calif.) according to the manufacturer's protocol with the following modification. Briefly, non-specific sites were blocked with a working solution of M.O.M. immunoglobulin blocking reagent for 1 hour at room temperature and washed twice for 2 minutes each. The slides were then incubated with M.O.M. diluent for 5 minutes at room temperature followed by incubation for 30 minutes at room temperature with mouse monoclonal anti-human Ki-67 antibody (1:100) (Dako, Carpinteria, Calif.) in M.O.M. diluent. Slides were washed with PBS for 2 minutes and incubated for 2 hours in PBS with a secondary antibody, goat anti-mouse IgG-rhodamine (Amersham Biosciences) (1:1,000) at 4° C. in the dark. The slides were then washed 3 times for 20 minutes each in PBS and mounted with Aqua Poly/Mount solution.

Cleaved Caspase-3 Immunoreactivity:

To evaluate apoptosis activity, tissues were reacted with a rabbit polyclonal antibody to cleaved caspase-3 (ASP 175; Cell Signaling Technology, Inc., Danvers, Mass.). Tissue sections were fixed in 4% formaldehyde for 15 minutes at 22° C. and then non-specific sites were blocked with PBS containing 5% normal goat serum (NGS) and 0.3% Triton X-100 for 1 hour. Sections were incubated with rabbit anti-cleaved caspase-3 antibody (1:200) diluted in PBS containing 3% NGS and 0.2% Triton-X 100, overnight at 4° C. The tissues sections were then washed for 30 minutes with PBS and incubated with a goat anti-rabbit IgG—rhodamine-conjugated secondary antibody (1:10,000) (Amersham Biosciences) diluted in PBS containing 3% NGS for 2 hours at room temperature in the dark. Slides were washed for 30 minutes and mounted with Aqua Poly/Mount solution.

Immunofluorescence was visualized and photographed using a Nikon Eclipse E400 upright fluorescent microscope and Nikon Coolpix 995 digital camera with 40× objective and 2 second exposures.

Treatment of Human Pancreatic Cells and Tumors with Gastrin siRNA Laden Nanoliposomes Cationic nanoliposomes were used as delivery vehicles for gastrin stealth siRNAs (Invitrogen) both in vitro and in vivo. Nanoliposomes (70 nm) were synthesized by combining 1,2-Dioleoyl-3-Trimethylammonium-Propane Chloride (DOTAP), 1,2-Dioleoyl-sn-Glycero-3-Phosphoethanolamine (DOPE), and 1,2-distearoyl-sn-glycero-3-phosphoethanolamine-N-[methoxy(polyethylene glycol)-2000] (DSPE-PEG 2000) (Avanti Polar Labs, Alabaster, Ala.) in chloroform at a 4.75:4.75:0.5 molar ratio. For in vitro experiments, BxPC-3 cells ($1.25 \times 10^5$) were treated with 65 µg/ml nanoliposomes loaded with 160 nmoles of a siRNA corresponding to the gastrin sh286 target site, nanoliposomes loaded with a gastrin sh286 scrambled control siRNA or with empty nanoliposomes. After 72 hours, RNA was extracted and analyzed by Real-Time RT-PCR as described above (N=12 replicates per group). For fluorescent liposome uptake experiments, empty liposomes were labeled with rhodamine, incubated in vitro with AsPC-1 cells for 1 hour, and immediately photographed using fluorescence microscopy (above).

For in vivo siRNA/nanoliposome treatments, AsPC-1 cells were injected ($10^6$ cells in 0.1 ml) subcutaneously into each flank of athymic nude mice. Starting on day 14 after tumor cell inoculation, when all mice had palpable tumors, animals were treated by tail vein injection (0.1 ml) every other day with one of the following: Group 1=empty nanoliposomes; Group 2=nanoliposomes with scrambled control siRNA, and Group 3=nanoliposomes laden with gastrin siRNA-286; (N=12 tumors per group). Tumor diameter was measured weekly with calibers. After 3 weeks of treatment, tumors from the control animals had reached the maximum allowable size (12 mm) and all mice were then necropsied.

Statistics

Tumor data were compared using pairwise Mann-Whitney tests on groups as indicated. Effects of gastrin suppression on tumor growth and metastases were analyzed using linear regression and both parametric and non-parametric (Spearman) correlation coefficients. Two-sided statistical tests were performed at the 0.05 significance level to assess the significance of the coefficients. For the Real-Time data, pairwise Student T-tests were performed on the normalized mean $\Delta C_T$ values for each group using a modified Bonferroni method to correct for multiple comparisons.

Liposome Characterization and siRNA Loading

A quasielastic light scattering system (Malvern Nanosizer, Malvern Instruments, UK) was used to measure particle diameter of nanoliposomes±siRNA 1-d. after preparation. Nanoliposomal loading of siRNA was measured by mixing fluorescent, Alexa Fluor 546 tagged siRNA (Qiagen, Valencia, Calif.) with nanoliposomes at specific weight ratios (1:5, 1:10, 1:15) and complexing at room temperature for 0.5, 3, or 6 hr. Loading was considered complete when no free siRNA was evident with complex remaining in well of a 2% agarose gel. To measure liposome-mediated protection of siRNA, nanoliposomes complexed with siRNA overnight were treated with 50% FBS for 10, 30, 60, 180, or 360 m. Following FBS treatment, half of the complex at each time point was treated with 0.5% SDS for 10 m. at 37° C. to disrupt the complexes and release free siRNA. siRNA alone was also digested with 50% FBS at each time point to serve as a control. All samples were run on a 2% agarose gel at 100 V. for 20 m. and visualized using UV.

Nanoliposomal Toxicity

To assess cytotoxicity of nanoliposomes complexed with siRNA in normal or cancer cells; $5 \times 10^3$ fibroblasts (FF2441), keratinocytes (HFK), melanocytes (melan-a), and melanoma (1205 Lu) cells were plated into 96-well plates and 48 hr. later treated with ghost nanoliposomes for 24 hr. at nanoliposomal concentrations of 12.5, 25, and 50 µM or exposed to 125, 250, 500, 1000, or 2000 nM of siRNA complexed with nanoliposomes and compared to untreated control cells. Cytotoxicity was analyzed using the Cell Titer 96 aqueous nonradioactive cell proliferation assay (Promega, Madison, Wis.).

APPENDIX "B"

It should be understood that the examples and embodiments described herein are for illustrative purposes only and that various modifications or changes in light thereof will be suggested to persons skilled in the art and are to be included within the spirit and purview of this application.

Example 1

```
Sequences for gastrin siRNAs:
  sh90                                        (SEQ ID NO: 1)
           GAUGCACCCUUAGGUACAG sh248                                       (SEQ ID NO: 2)
           AGAAGAAGCCUAUGGAUGG sh286                                       (SEQ ID NO: 3)
           GUGCUGAGGAUGAGAACUA
```

Example 2

| | |
|---|---|
| GASTRIN | NUCLEOTIDE SEQUENCE |
| LOCUS | NM_000805    440 bp mRNA linear PRI 25-May-2008 |
| DEFINITION | Homo sapiens gastrin (GAST), mRNA. |
| ACCESSION | NM_000805 |
| VERSION | NM_000805.3 GI:68215467 |
| KEYWORDS | |
| SOURCE | Homo sapiens (human) ORGANISM Homo sapiens Eukaryota; Metazoa; Chordata; Craniata; Vertebrata; Euteleostomi; Mammala; Eutheria; Euarchontoglires; Primates; Haplorrhini; Catarrhini; Hominidae; Homo. |
| REFERENCE | 1 (bases 1 to 440) |
| AUTHORS | Zhang, Z.H., Wu, S.D., Su, Y., Jin, J.Z., Fan, Y., Yu, H. and Zhang, L.K. |
| TITLE | Differences and significance of motilin, vasoactive intestinal peptide and gastrin in blood and gallbladder tissues of patients with gallstones |
| JOURNAL | HBPD INT 7 (1), 58-64 (2008) |
| PUBMED | 18234640 |
| REMARK | GeneRIF: The abnormal excretion of hormonal factors is closely related to gallstone formation |
| REFERENCE | 2 (bases 1 to 440) |
| AUTHORS | Ansorge, N., Juttner, S., Cramer, T., Schmidt, W.E., Hocker, M. and Schmitz, F. |
| TITLE | An upstream CRE-E-box element is essential for gastrin-dependent activation of the cyclooxygenase-2 gene in human colon cancer cells |
| JOURNAL | Regul. Pept. 144 (1-3), 25-33(2007) |
| PUBMED | 17604853 |
| REMARK | GeneRIF: description of the gastrin evoked effects on the transcriptional activity of the COX-2 gene in colorectal cancer cells and the identification of regulatory promoter elements. |
| | REFERENCE 3 (bases 1 to 440) |
| | AUTHORS Stone, S.R., Mierke, D.F. and Jackson, G.E. |
| TITLE | Evidence for a C-terminal structural motif in gastrin and its bioactive fragments in membrane mimetic media |
| JOURNAL | Peptides 28 (8), 1561-1571 (2007) |
| PUBMED | 17698249 |

| | | |
|---|---|---|
| | REMARK | GeneRIF: possible biologically relevant structural motif for gastrin activity |
| | REFERENCE | 4 (bases 1 to 440) |
| AUTHORS | | Tu, S., Chi, A.L., Lim, S., Cui, G., Dubeykovskaya, Z., Ai, W., Fleming, J.V., Takaishi, S. and Wang, T.C. |
| TITLE | | Gastrin regulates the TFF2 promoter through gastrin-responsive cis-acting elements and multiple signaling pathways |
| | JOURNAL | Am. J. Physiol. Gastrointest. Liver Physiol. 292 (6), G1726-G1737 (2007) |
| | PUBMED | 17332476 |
| REMARK | | GeneRIF: Gastrin regulates TFF2 transcription through a GC-rich DNA-binding site and a protein kinase dependent pathway. |
| REFERENCE | | 5 (bases 1 to 440) |
| AUTHORS | | Stephens, M.R., Hopper, A.N., Lewis, W.G., Blackshaw, G., Edwards, P., Osborne, B. and Thompson, I.W. |
| TITLE | | Prognostic significance of gastrin expression in patients undergoing R0 gastrectomy for adenocarcinoma |
| JOURNAL | | Gastric Cancer 10 (3), 159-166 (2007) |
| PUBMED | | 17922093 |
| REMARK | | GeneR1F: The duration of survival of patients whose tumors exhibited well-differentiated gastrin-positive tumor (GPT) cells (n = 12) was significantly poorer than that of patients whose tumors were GPT-negative (5-year survival, 30% vs 54%; P = 0.037). |
| REFERENCE | | 6 (bases 1 to 440) |
| AUTHORS | | Pauwels, S., Najdovski, T., Dimaline, R., Lee, G.M. and Deschodt-Lanckman, M. |
| TITLE | | Degradation of human gastrin and CCK by endopeptidase 24.11: differential behaviour of the sulphated and unsulphated peptides |
| JOURNAL | | Biochim. Biophys. Acta 996 (1-2), 82-88 (1989 |
| PUBMED | | 2736261 |
| REFERENCE | | 7 (bases 1 to 440) |
| AUTHORS | | Higashimoto, Y., Himeno, S., Shinomura, Y., Nagao, K., Tamura, T. and Tarui, S. |
| TITLE | | Purification and structural determination of urinary NH2-terminal big gastrin fragments |
| JOURNAL | | Biochem. Biophys. Res. Commun. 160 (3), 1364-1370 (1989) |
| PUBMED | | 2730647 |
| REFERENCE | | 8 (bases 1 to 440) |
| AUTHORS | | Lund, T., Geurts van Kessel, A.H., Haun, S. and Dixon, J.E. |
| TITLE | | The genes for human gastrin and cholecystokinin are located on different chromosomes |
| JOURNAL | | Hum. Genet. 73 (1), 77-80 (1986) |
| PUBMED | | 3011648 |
| REFERENCE | | 9 (bases 1 to 440) |
| AUTHORS | | Polosatov, M .V., Klimov, P.K., Masevich, C.G., Samartsev, M.A. and Wunsch, E. |
| TITLE | | Interaction of synthetic human big gastrin with blood proteins of man and animals |
| JOURNAL | | Acta Hepatogastroenterol (Stuttg) 26 (2), 154-159 (1979) |
| PUBMED | | 463490 |
| REFERENCE | | 10 (bases 1 to 440) |
| AUTHORS | | Fritsch, W. P., Hausamen, T.U. and Scholten, T. |
| TITLE | | [Gastrointestinal hormones. I. Hormones of the gastrin group] |
| JOURNAL | | Z Gastroenterol 15 (4), 264-276 (1977) |
| PUBMED | | 871064 |
| COMMENT | | REVIEWED REFSEQ: This record has been curated by NCBI staff. The reference sequence was derived from BC069724.1 and BM768483.1. On Jun. 24, 2005 this sequence version replaced gi:6005999. |

Summary: Gastrin is a hormone whose main function is to stimulate secretion of hydrochloric acid by the gastric mucosa, which results in gastrin formation inhibition. This hormone also acts as a mitogenic factor for gastrointestinal epithelial cells. Gastrin has two biologically active peptide forms, G34 and G17.

Publication Note: This RefSeq record includes a subset of the publications that are available for this gene. Please see the Entrez Gene record to access additional publications.

COMPLETENESS: complete on the 3' end.

| PRIMARY REFSEQ_SPAN | PRIMARY_IDENTIFIER | PRIMARY_SPAN COMP |
|---|---|---|
| 1-410 | BC069724.1 | 1-410 |
| 411-440 | BM768483.1 | 445-474 |

FEATURES        Location/Qualifiers
source  1..440
    /organism= "Homo sapiens"
    /mol_type= "mRNA"
    /db_xref= "taxon:9606"
    /chromosome= "17"
    /map= "17q21"
gene    1..440
    /gene= "GAST"
    /synonym= "GAS"
    /note= "gastrin"
    /db_xref= "GeneID:2520"
    /db_xref= "HGNC:4164"
    /db_xref= "HPRD:00671"
    /db_xref= "MIM: 137250"
    exon 1..27
    /gene= "GAST"
    /inference= "alignment:Splign"
    /number=1
        STS 3..404
        /gene= "GAST"
    /db_xref="UniSTS:483807"
exon    28..243
    /gene= "GAST"
    /inference= "alignment:Splign"
    /number=2
CDS     33..338
    /gene= "GAST"
    /codon_start=1
    /product= "gastrin preproprotein"
    /protein_id= "NP 000796.1"
    /db_xref= "G I :4503923"
    /db xref= "CCDS:CCDS11404.1"
    /db_xref= "GeneID:2520"
    /db_xref= "HGNC:41 64"
    /db xref= "HPRD:00671"
    /db xref= "MIM:137250"
    /translation= "MQRLCVYLIFALALAAFSEASWKPRSQQPDAPLGTGA
NRDLELPWLEQQGPASHHRRQLGPQGPPHLVADPSKKQGPWLEEE
EEAYGWMDFGRRSAEDEN" (SEQ ID NO: 6)
    sig peptide 33..89
        /gene= "GAST"
    proprotein 90..335
        /gene= "GAST"
        /product= "gastrin proprotein"
    mat peptide 207..308
        /gene= "GAST"
        /product= "gastrin G34"
    mat peptide 258..308
        /gene= "GAST"
        /product= "gastrin G 17"
    STS     80..312
        /gene= "GAST"
        /standard name= "GAS"
        /db_xref= "UniSTS:253979"
exon    244..435
    /gene= "GAST"
    /inference= "allgnment:Splign"
        /number=3
polyA sianal 415. .420
        /gene= "GAST"
polyA site 435
        /gene= "GAST"

Origin (SEQ ID NO: 7)
```
  1  ggcaccacac acctcccagc tctgcagacg agatgcagcg actatgtgtg tatgtgctga
 61  tctttgcact ggctctggcc gccttctctg aagcttcttg gaagccccgc tcccagcagc
121  cagatgcacc cttaggtaca ggggccaaca gggacctgga gctaccctgg ctggagcagc
181  agggcccagc ctctcatcat cgaaggcagc tgggacccca gggtccccca cacctcgtgg
241  cagacccgtc caagaagcag ggaccatggc tggaggaaga agaagaagcc tatggatgga
301  tggacttcgg ccgccgcagt gctgaggatg agaactaaca atcctagaac 5 caagcttcag
361  agcctagcca cctcccaccc cactccagcc ctgtcccctg aaaaactgat caaaaataaa
421  ctagtttcca gtggaaaaaa
```

---

We claim:

1. A method of inhibiting in vivo gastrin production in gastrin mediated cancers by introducing into the gastrin producing cancer cells an siRNA polynucleotide that targets regions of the gastrin encoding mRNA sequence at position 90 or position 286.

2. The method of claim 1 in which the siRNA comprises one or more of the following siRNA sequences:

GAUGCACCCUUAGGUACAG (SEQ ID NO: 1)

GUGCUGAGGAUGAGAACUA. (SEQ ID NO: 3)

3. The method of claim 1 in which the gastrin producing cancer cell is a pancreatic cancer cell.

4. The method of claim 3 in which siRNA GUGCUGAG-GAUGAGAACUA (SEQ ID NO: 3) is introduced into the pancreatic cancer cells.

5. The method of claim 1 in which the siRNA polynucleotide that targets regions of the gastrin encoding mRNA is introduced into the gastrin producing cancer cell by a nanoliposome.

6. The method of claim 5 in which the nanoliposome is complexed with an effective amount of PEG.

* * * * *

SEQUENCE LISTING

<160> NUMBER OF SEQ ID NOS: 7

<210> SEQ ID NO 1
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1
gaugcacccu uagguacag                                                      19

<210> SEQ ID NO 2
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 2
agaagaagcc uauggaugg                                                      19

<210> SEQ ID NO 3
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 3
gugcugagga ugagaacua                                                      19

<210> SEQ ID NO 4
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
cagcgactat gtgtgtatgt gctg                                                24

<210> SEQ ID NO 5
<211> LENGTH: 21
<212> TYPE: DNA

```
<213> ORGANISM: Artificial Sequence
<220> FEATURE:
<223> OTHER INFORMATION: Description of Artificial Sequence: Synthetic
      primer

<400> SEQUENCE: 5
gaagtccatc catccatagg c                                                  21

<210> SEQ ID NO 6
<211> LENGTH: 101
<212> TYPE: PRT
<213> ORGANISM: Homo sapiens

<400> SEQUENCE: 6

Met Gln Arg Leu Cys Val Tyr Val Leu Ile Phe Ala Leu Ala Leu Ala
1               5                   10                  15

Ala Phe Ser Glu Ala Ser Trp Lys Pro Arg Ser Gln Gln Pro Asp Ala
            20                  25                  30

Pro Leu Gly Thr Gly Ala Asn Arg Asp Leu Glu Leu Pro Trp Leu Glu
        35                  40                  45

Gln Gln Gly Pro Ala Ser His His Arg Arg Gln Leu Gly Pro Gln Gly
    50                  55                  60

Pro Pro His Leu Val Ala Asp Pro Ser Lys Lys Gln Gly Pro Trp Leu
65                  70                  75                  80

Glu Glu Glu Glu Glu Ala Tyr Gly Trp Met Asp Phe Gly Arg Arg Ser
                85                  90                  95

Ala Glu Asp Glu Asn
            100

<210> SEQ ID NO 7
<211> LENGTH: 440
<212> TYPE: DNA
<213> ORGANISM: Homo sapiens

<400> SEQUENCE: 7
ggcaccacac acctcccagc tctgcagacg agatgcagcg actatgtgtg tatgtgctga        60
tctttgcact ggctctggcc gccttctctg aagcttcttg gaagcccgc  tcccagcagc       120 cagatgcacc cttaggtaca ggggccaaca gggacctgga gctaccctgg ctggagcagc       180
agggcccagc ctctcatcat cgaaggcagc tgggacccca gggtccccca cacctcgtgg       240
cagacccgtc caagaagcag ggaccatggc tggaggaaga agaagaagcc tatggatgga       300
tggacttcgg ccgccgcagt gctgaggatg agaactaaca atcctagaac caagcttcag       360
agcctagcca cctcccaccc cactccagcc ctgtcccctg aaaaactgat caaaaataaa       420
ctagtttcca gtggaaaaaa                                                  440
```